United States Patent
Li

(10) Patent No.: US 12,344,639 B2
(45) Date of Patent: Jul. 1, 2025

(54) CHIMERIC GAS VESICLE AND PROTEIN EXPRESSION SYSTEM THEREFOR

(71) Applicant: Gasilus Pharmaceuticals, Inc., Hayward, CA (US)

(72) Inventor: Ning Li, Foster City, CA (US)

(73) Assignee: GASILUS PHARMACEUTICALS, INC., Hayward, CA (US)

( * ) Notice: Subject to any disclaimer, the term of this patent is extended or adjusted under 35 U.S.C. 154(b) by 200 days.

(21) Appl. No.: 17/749,615

(22) Filed: May 20, 2022

(65) Prior Publication Data

US 2022/0372085 A1 Nov. 24, 2022

Related U.S. Application Data

(60) Provisional application No. 63/191,902, filed on May 21, 2021.

(51) Int. Cl.
*C12N 15/70* (2006.01)
*C07K 14/32* (2006.01)
*C12N 15/62* (2006.01)

(52) U.S. Cl.
CPC .............. *C07K 14/32* (2013.01); *C12N 15/62* (2013.01); *C07K 2319/735* (2013.01)

(58) Field of Classification Search
CPC ... C07K 14/32; C07K 2319/735; C12N 15/62
See application file for complete search history.

(56) References Cited

FOREIGN PATENT DOCUMENTS

| WO | WO-9720854 A1 | * | 6/1997 | ........... A61K 39/385 |
| WO | WO-2020146379 A1 | * | 7/2020 | ........... A61K 49/223 |

OTHER PUBLICATIONS

Felicitas Pfeifer, Distribution, formation and regulation of gas vesicles, Nature Reviews Microbiology, vol. 10, Oct. 2012 705.

* cited by examiner

*Primary Examiner* — Lianko G Garyu
*Assistant Examiner* — Kristina M Hellman
(74) *Attorney, Agent, or Firm* — troutman pepper locke; Tim Tingkang Xia, Esq.

(57) ABSTRACT

The present disclosure features the chimeric gas vesicle (CGV) and its expression in *E. coli*. The chimeric gas vesicle comprises two or more gas vesicle rib proteins. The heterologous peptides, 6-AA to 56-AA long, can be inserted into one recombinant rib protein in frame. The resulting CGV carrying the heterologous peptide can be used in many applications.

5 Claims, 11 Drawing Sheets

Specification includes a Sequence Listing.

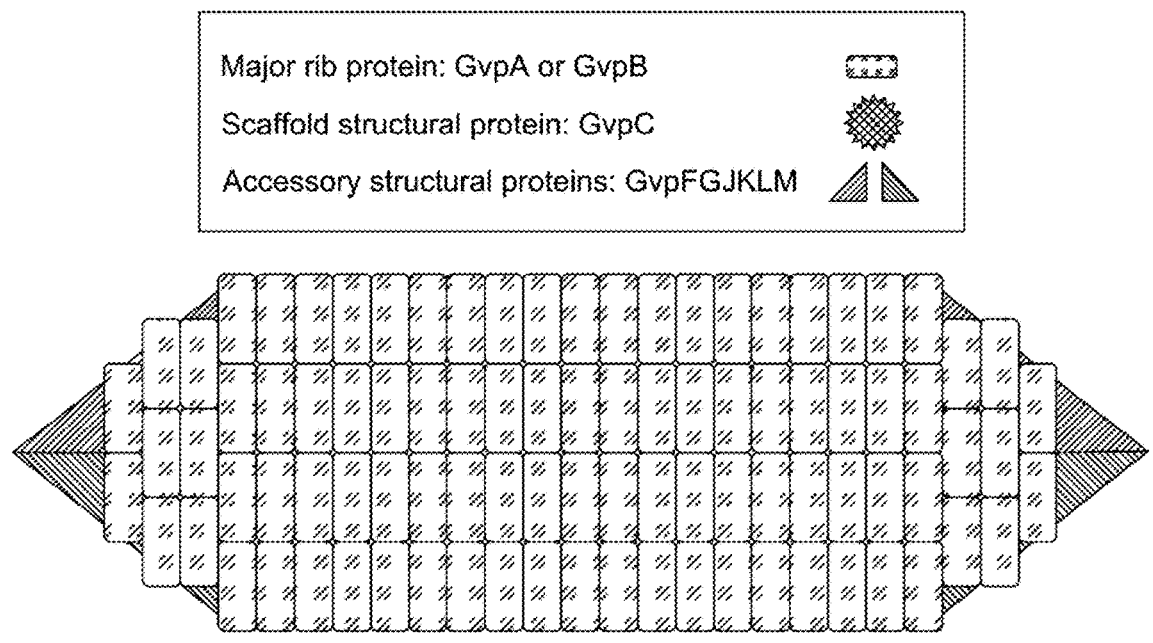
(Gas vesicle in halobacteria, cyanobacteria, *P. megaterium* or *E. coli*)
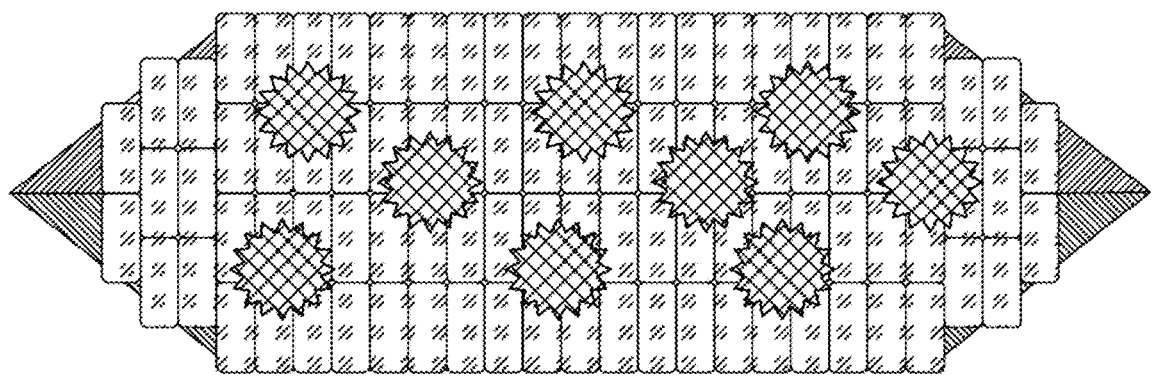
(Gas vesicle in halobacteria and cyanobacteria)
FIG. 1

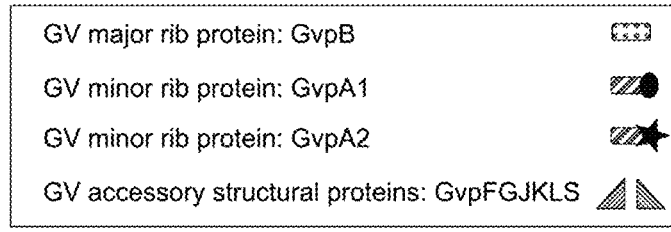
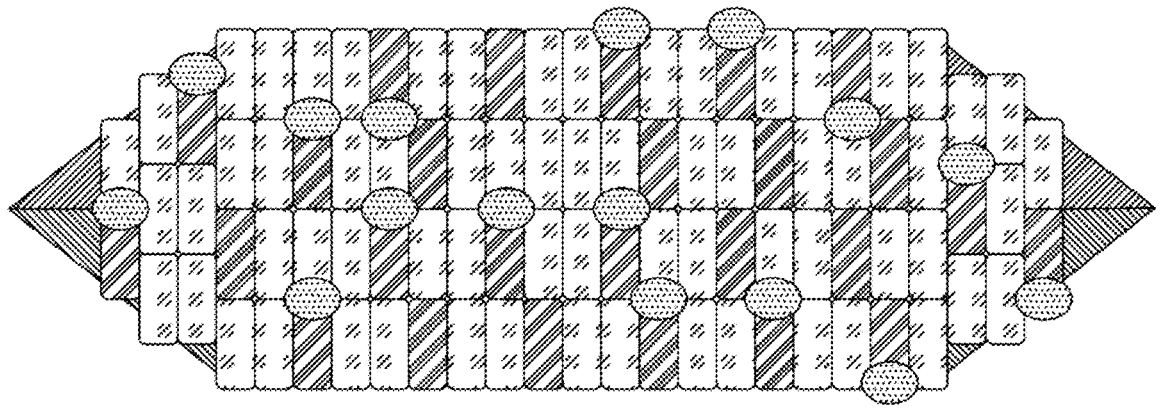
(Chimeric as vesicle without GvpC in *P. megaterium* or *E. coli*)
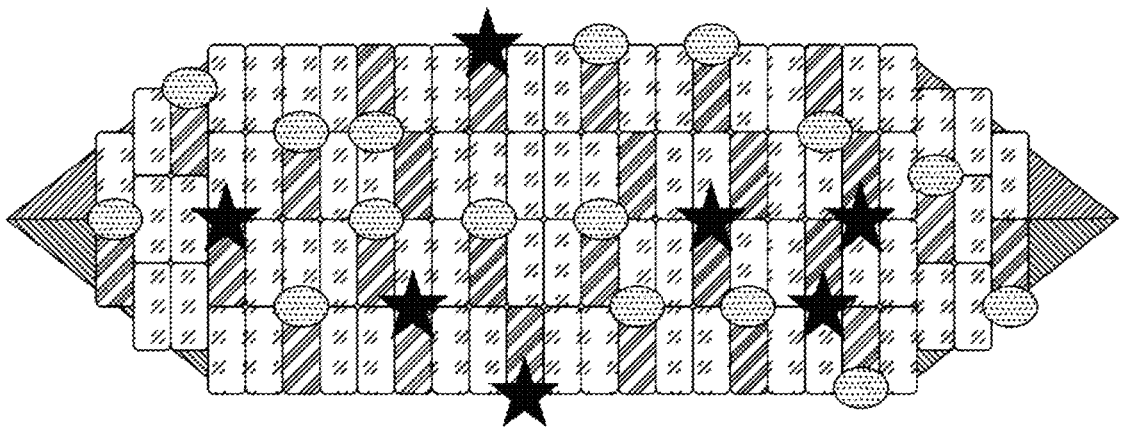
(Chimeric gas vesicle with two or more minor rib proteins in *P. megaterium* or *E. coli*)
FIG. 3

| | | |
|---|---|---|
| Priestia megaterium GvpA | MSIQKSTDSSSLAEVIDRILDKGIVIDAFARVSLVGIELLLTIEARVVIASVDTWLRYAEA | 60 |
| Priestia megaterium GvpB | MSIQKSTNSSSLAEVIDRILDKGIVIDAFARVSLVGIELLLTIEARVVIASVDTWLRYAEA | 60 |
| Anabaena flos-aquae | -AVEKTNSSSLAEVIDRILDKGIVIDAFARVSVVGIELLLTIEARVLA EARIVIASVETYLKYAEA | 59 |
| Halobacterium salinarum c-vac | ---MAQPDSSSLAEVIDRVLDRVLDKGVVVWARISLVGIETLLTVEARVVAASVDTFLHYAEE | 57 |
| Halobacterium salinarum p-vac | ---MAQPDSSGLAEVLDRVLDKGVVVWARVSLVGIETLLTVEARVVAASVDTFLHYAEE | 57 |
| | HHHHHHHHHH SSSSSSSSSSS SSSSSSSSSS HHHHHHHHH | |
| | α-helix   β-sheet   β-sheet   α-helix | |

Core sequence

| | | |
|---|---|---|
| Priestia megaterium GvpA | VGLLTDKVEEEGLPGRTEERGAGLSF-- | 86 (SEQ ID NO.: 1) |
| Priestia megaterium GvpB | VGLLRDDVEENGLPERSNSSEGQPRFSI | 88 (SEQ ID NO.: 2) |
| Anabaena flos-aquae | VGLTQSAAVPA----------------- | 70 (SEQ ID NO.: 47) |
| Halobacterium salinarum c-vac | IAKIEQAELTAGAEAPEPAPEA------ | 79 (SEQ ID NO.: 48) |
| Halobacterium salinarum p-vac | IAKIEQAELTAGARRHPRPDAQASLRPA | 85 (SEQ ID NO.: 49) |

FIG. 4a

Priestia megaterium GvpA    MSIQKSTDSSSSLAEVIDRILDKGIVIDAFARVSLVGIETLLTEARVVIASVDTWLRYAEA 60
Priestia megaterium GvpB    MSIQKSTNSSSLAEVIDRILDKGIVIDAFARVSVGIETLLTEARVVIASVDTWLRYAEA 60
                            HHHHHHHHH SSSSSSSSSS      SSSSSSSSSS  HHHHHHHHH
                             α-helix     β-sheet          β-sheet      α-helix
                            ―――――――――――――――――――――――――――――――――――――――――――
                                              Core sequence Priestia megaterium GvpA    VXXXXXXXXXXXXXXXXXXXXXXXXXXXXXXXXXXXX 61-117 AA or more (SEQ ID NO.: 50)
Priestia megaterium GvpB    VXXXXXXXXXXXXXXXXXXXXXXXXXXXXXXXXXXXX 61-117 AA or more (SEQ ID NO.: 51)
                            ―――――――――――――――――――――――――――――――――――――――
                            6 to 56-AA or more heterologous peptide

FIG. 4b

S1 — Construction of plasmid:
a plasmid is constructed by inserting a DNA sequence encoding a heterologous peptide having 6 to 56 amino acids or above in-frame at the C-terminus and/or N-terminus of the genetically engineered GvpA or GvpB protein in a recombinant *gvp* operon derived from P. megaterium by PCR and Gibson Assembly.

S1.1 — Sequence validation:
The plasmid sequence with desired insertion is confirmed by DNA sequencing.

S2 — Transformation of plasmid:
the constructed plasmid is transformed into *E. coli* or other suitable bacteria hosts capable of expression and production of CGV.

S3 — Induction:
the transformant is grown in a proper environment to an optimal condition for inducing protein expression. The transformant is stimulated with IPTG (Isopropyl β-d-1-thiogalactopyranoside) or other inducers for the expression of the CGV.

S4 — Purification and quantification of the CGV.

FIG. 9

Purification and quantification of CGV-Covid-19 vaccine in PBS.

↓

Administration of the CGV-Covid-19 vaccine into the subject in need.

↓

Detection of the immune responses.

FIG. 10

CHIMERIC GAS VESICLE AND PROTEIN EXPRESSION SYSTEM THEREFOR

CROSS REFERENCE TO RELATED APPLICATION

This application claims the benefit of provisional application Ser. No. 63/191,902, filed May 21, 2021.

FIELD OF THE INVENTION

The invention is related to chimeric gas vesicles (CGVs) and uses thereof.

BACKGROUND OF THE INVENTION

Gas vesicles are intracellular, protein-coated and hollow organelles found in cyanobacteria, soil bacteria and halophilic archaea. They are permeable to ambient gases by passive diffusion and provide buoyancy which enables bacteria cells to adjust their vertical position in aqueous environments for access of oxygen and light.

Gas vesicles are cylindrical-shaped with conical-ends nanostructures of 40 to 250 nm in width and 50 to 1000 nm in length. The discrete protein nanoparticles with permeability to ambient gas provides great potential for bioengineering for a variety of applications. Development of biological imaging under resonance and expansion of biomass production counting on its positive increase of buoyancy has been described in a variety of prior arts. Besides, the nano-scale bio-particles are desirable vehicles for vaccines.

Disclosed in Pat. WO1990010071A1 are recombinant cells and a recombinant vector for gas vesicle protein expression in E. coli and improvement of floatation properties of the transformed cells. Bacillus thuringiensis israelensis (Bti) is a group of bacteria which can be used as biological control agents for larvae stages of certain dipterans. When transformed with gas vesicle genes, the tendency of Bti to settle in water is reduced and its larvicidal activity becomes more persistent. Other hosts overcome sedimentation problems in bio-reactors with incorporation of gas vesicle genes, which improves bio-degradation of organic wastes or medical/agricultural products.

In Pat. WO2018043716A1, Mizushima and Watanabe published a method for introducing gas vesicle genes including gvpA and gvpC into eukaryotic cells for gas vesicle protein expression. The gvpA and gvpC genes are derived from cyanobacteria and featured with optimized codons for mammalian expression. A transposon vector serves as the vehicle of gvpA and gvpC genes for introduction of genes into mammalian cells. The method disclosed in this prior art also provides a kit for establishing a stable clone or a transgenic animal for constant production of gas vesicles.

In US Pat. US20140234904A1, Stephen and Levi disclosed methods for harvesting photosynthetic unicellular organisms and the formation of gas vesicles in the photosynthetic unicellular organisms. The self-assembling gas vesicle proteins form conical filaments which are capable of blocking water molecules but allow the diffusion of gas. Overexpression of the gas vesicle increases positive buoyancy of the photosynthetic unicellular organisms and allows for harvesting without the need for centrifugation, filtration, or chemical flocculation.

Shapiro et al (Science 27 Sep. 2019: Vol. 365, Issue 6460, pp. 1469-1475) described a protocol for gas vesicle isolation and functionalization. The nanostructures of gas vesicles are modified with moieties for targeting and fluorescence, and using ultrasound and magnetic resonance for imaging. It takes 3 to 8 days for preparation of these genetically encodable nanostructures, and the nanostructures enable multi-modal and noninvasive biological imaging featuring high sensitivity and potential for molecular targeting.

In Pat. WO2021041934A1, Jin et al disclosed an engineered protease sensitive gas vesicle. The engineered protease sensitive gas vesicle comprises a GvpA or GvpB protein and an engineered GvpC protein. Protease recognition sites are inserted within a central portion of the GvpC or attached to the N or C-terminus of the GvpC. The engineered gas vesicles exhibit an ultrasound response with baseline nonlinearity to collapse. Proteases bind to the recognition sites and result in cleavage thereof. Subsequently the engineered gas vesicles collapse following the cleavage and detection of the collapses is for screening engineered protease sensitive gas vesicles. The method enables reduction of collapse pressure profile, protease degradation, and sufficient protein yield is obtained with improvement of engineered gas vesicle expression in host cells. Also, ultrasound applied to obtain detection and sensing presents an enhanced nonlinear behavior.

In US Pat. U.S. Pat. No. 5,824,309, DasSarma et al disclosed a method for producing protein vaccines by utilizing recombinant gas vesicles. Foreign epitopes derived from pathogens are inserted into gvpA or gvpC for antigen presenting to elicit immunogenicity of subjects upon administration. In absence of an adjuvant, vaccination with the recombinant gas vesicles result in long-lasting immunoglobulin IgG or IgM responses. Archaeon cells *Halobacterium halobium* are cultured as a host for the engineered gas vesicle preparation.

Majority of GV research was conducted in halobacteria, cyanobacteria and *Priestia megaterium* (previously known as *Bacillus megaterium*).

In cyanobacteria and halobacteria, the lipid-free, rigid proteinaceous membrane consists exclusively of proteins: the major hydrophobic 70 to 85 amino acid (AA) GvpA protein, which forms GV ribbed basic structure, and a minor constituent, hydrophilic 200- to 450-AA GvpC, located on the GV outer surface as shown in FIG. 1. GvpC is called scaffold structural protein as its role in strengthening the GV structure. In soil bacteria *P. megaterium*, an 88-AA GvpB protein, homologous to GvpA of cyanobacteria and halobacteria, is found necessary for the GV formation and play the role as GvpA of cyanobacteria and halobacteria. An extra copy of gvpA gene, homologous to gvpB in *P. megaterium* is present in the 14 gyp gene operon in *P. megaterium* as shown in FIG. 6 and its role is not determined. No GvpC homolog is present in *P. megaterium*.

Besides the major GV structural protein GvpA and minor GV scaffold structural protein GvpC, five accessory GV proteins: GvpJ, GvpM, GvpF, GvpG, GvpL are detected by immunoblotting in the GV of halobacteria as indicated in FIG. 1. These accessory Gyp proteins constitute a very small portion of total GV protein and are hypothesized to influence the GV curvature or localized to the conical tips of GV. In the cyanobacterium *A. flos-aquae*, GvpJ, GvpK and GvpL homologs have been identified, while in *P. megaterium*, all five accessory GV protein homologs have been identified.

Gas vesicle protein A (GvpA) is the major structural protein of gas vesicles and constitutes the majority (97%) of the gas vesicle wall. The wall is 2 nm thick and consists of a single layer of GvpA. GvpA forms 4.6 nm 'ribs' that run nearly perpendicular to the long axis of the gas vesicle. As demonstrated in FIG. 4a, GvpA has a hydrophobic α-helix, β-sheet, β-sheet and α-helix core amino acid sequence (GvpA core sequence).

GvpA protein encoded by gvpA genes from several dozens of different microorganisms are sequenced and identified. The GvpA protein sequences are highly homologous, especially in the α-helix, β-sheet, β-sheet and α-helix core sequence as indicated in FIG. 4a. The N- and C-terminal sequences of GvpA vary among different species.

Multiple identical copies of gvpA gene are found in some cyanobacteria, two copies of slightly different gvpA gene are found on two gyp operons located on its chromosome and plasmid separately in halobacteria (c-vac and p-vac) and on a 14 gene gyp operon in *P. megaterium* (gvpA and gvpB).

It has been long recognized by the research field that there is only one kind of rib protein GvpA in each gas vesicle. In *Halobacterium salinarum*, c-vac and p-vac are located on different gene clusters at chromosome or plasmid respectively. The expression of c-vac and p-vac is under control by different mechanisms and thus the gas vesicle formed with either GvpA from c-vac or GvpA from p-vac at one time, not both. In *P. megaterium*, gvpA and gvpB are on the same 14-gene gyp operon. Only gvpB is needed to form the gas vesicle and the role of gvpA is unclear.

Attempts are made to modify GvpA by insertion of heterologous peptide sequence into the N-terminal, C-terminal, or core sequence of GvpA. However, the rigid nature of GvpA protein limits the capacity of GvpA modification. DasSarma's group revealed that in-frame attachment of more than 5 heterologous amino acids to the C-terminal of GvpA in *H. salinarum* result in its incapability of forming gas vesicles. Other insertion attempts at N-terminal, and core sequence of GvpA are failed as well. This limits the use of gas vesicles in various applications such as vaccines, biomarkers, etc.

GvpC is a minor scaffold structural protein and found on the gas vesicle surface in cyanobacteria and halophilic archaea. It accounts for 2.9% of total protein content of gas vesicles from *Anabaena flos-aquae* and it can be stripped from gas vesicles by detergent or the change of salt concentration. It is a scaffold protein which stabilizes gas vesicles through protein-protein interaction with GvpA. Attachment of heterologous peptides to GvpC can be up to 398 amino acids long in *H. salinarum*, which makes GvpC more applicable in bioengineering. The gas vesicles with the modification of GvpC are called gas vesicle nanoparticles (GVNPs).

Nonetheless, attachment of GvpC to gas vesicles is not stable and the ratio of GvpC/GvpA or GvpC/GV in gas vesicles is difficult to maintain constant in practice. For instance, the GVNP produced by halobacteria could only maintain stability in a high-salt environment. In a low-salt environment, GVNPs tend to break down its structure and GvpC detaches from the nanoparticles. Instability of GVNP and disassociation of GvpC from GVNP undermines the reliability of GVNPs as an antigen-presenting vehicle or imaging biomarker particles for ultrasound and MRI exam.

In another aspect, the production cycle of gas vesicles in halobacteria is 3 to 4 weeks long and time-consuming, therefore the GV/GVNP production cost in halobacteria is way higher than using the *E. coli* expression system. Also there is lack of an efficient vector/host system for GV expression and production in halobacteria.

Thus, a new form of genetically engineered chimeric gas vesicle (CGV) is desired to overcome these limitations.

SUMMARY OF THE INVENTION

In the gas vesicle research field, it is widely believed that only one protein, GvpA, forms the rib of the gas vesicle. In other words, in a given gas vesicle, there is only one kind of rib protein such as GvpA from cyanobacteria, halobacteria and soil bacteria, or its homolog GvpB from *P. megaterium*. In the present invention, a chimeric gas vesicle (CGV) involving two or more kinds of rib proteins is disclosed.

The advantages of the chimeric gas vesicles (CGVs) of the present invention over traditional GVs and GVNPs are numerous. For example, previous attempts of direct genetic modification of GvpA in GVs are unsuccessful due to rigidity of GvpA in the GVs, and only a limited number of heterologous peptides can be inserted without the destruction of the GV. The CGV disclosed in the present invention overcomes these limitations and makes the gas vesicle more versatile for various applications. In halobacteria, the genetically modified GvpC of GVNP attaches to GV via protein-protein interaction, which is vulnerable to thermohaline fluctuations and makes GvpC easy to fall off from GVNP. In the present invention, the heterologous peptide inserted in the CGV is covalently fused within the rib protein, which eliminates the fall-off problem of the heterologous peptide present on the CGV. Further, the process for making the CGV can be accomplished within a very short time period, which drastically reduces the production cycle time compared to the time required to make GVNPs in halobacteria or GVs in cyanobacteria. The CGVs are more stable than any other GVs previously described. In other words, the CGVs of the present invention have a higher "critical collapse pressure" than the traditional GVs. In some examples, the CGVs are stable at room temperature for at least one month and at 4° C. for at least six months without any degradation.

BRIEF DESCRIPTION OF THE DRAWINGS

FIG. 1 is a cartoon graph to illustrate native gas vesicle as previously discovered.

FIG. 3 is a cartoon graph to illustrate CGVs with heterologous peptides.

FIG. 4a shows alignment of gas vesicle rib proteins.

FIG. 4b shows alignment of recombinant minor rib protein with heterologous peptide.

FIG. 9 is a flowchart illustrating a method for producing a chimeric gas vesicle (CGV).

FIG. 10 is a flowchart illustrating a method for eliciting immune response by administrating CGV-Covid-19 to a subject in need.

DETAILED DESCRIPTION OF THE INVENTION

In the gas vesicle research field, as shown in FIG. 1, it is widely believed that only one protein, GvpA, forms the rib of the gas vesicle. In other words, in a given gas vesicle, there is only one kind of rib protein GvpA, such as from cyanobacteria, halobacteria and soil bacteria, or its homolog GvpB from *P. megaterium*, to be found.

Figure 2:
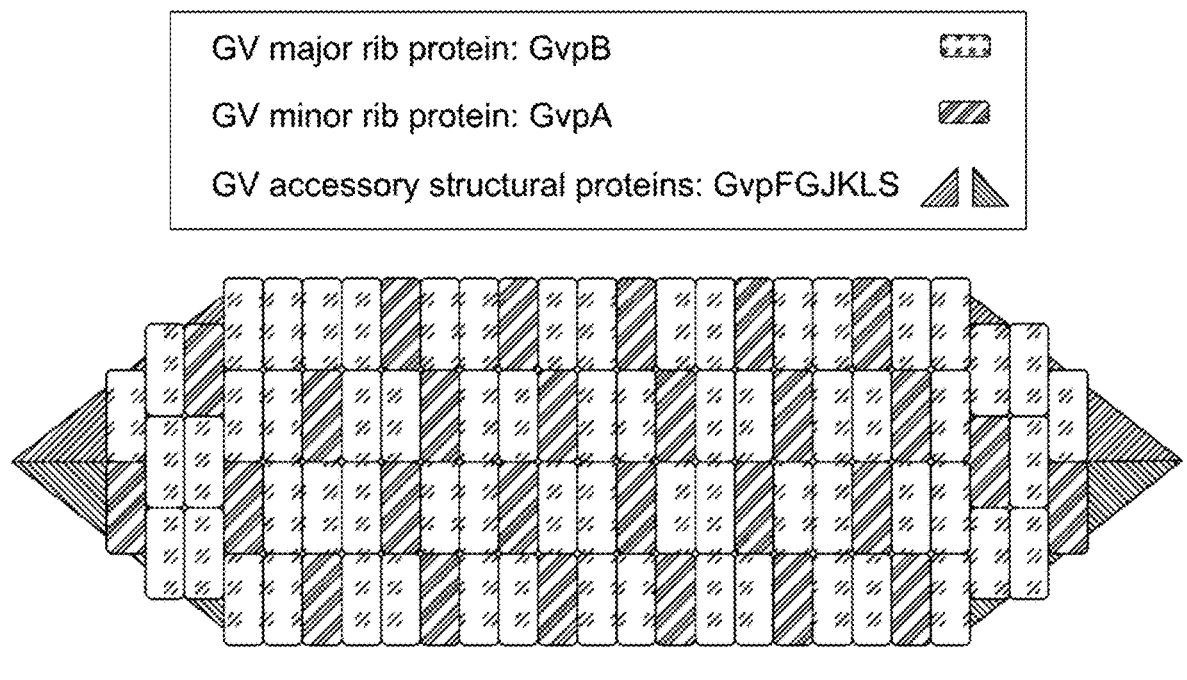
FIG. 2 is a cartoon graph to illustrate chimeric gas vesicle (CGV) with two or more different kinds of gas vesicle rib proteins in the present invention.

In one aspect, the present invention provides a chimeric gas vesicle comprising at least two Gyp rib proteins, wherein the rib protein is selected from a group consisting of a major rib protein and a minor rib protein, and wherein the major rib protein differentiates from the minor rib protein in that the major rib protein is capable of forming a gas vesicle independently. Preferably, as shown in FIGS. 2 and 3, there is less than 95% homology between the major rib protein and the minor rib protein, and the Gyp rib protein is derived from *P. megaterium*.

In exemplary embodiments, the at least two Gyp rib protein can be two major rib proteins, two minor rib proteins or a combination of one major rib protein and one minor rib protein. Preferably, the minor rib protein forms a complete CGV when the major rib protein is present, and under such circumstances the CGV is more stabilized.

In various embodiments, the major rib protein and the minor rib protein constitute at least 90% of the chimeric gas vesicle by dry weight.

In one or various embodiments, the minor rib protein comprises a core sequence and a heterologous peptide inserted in frame at C-terminus or N-terminus of the core sequence, wherein the core sequence is characterized by a protein structure comprising a first alpha helix, a first beta sheet at C-terminus of the first alpha helix; a second beta sheet at C-terminus of the first beta sheet; and a second alpha helix at C-terminus of the second beta sheet.

In preferred embodiments, the core sequence is selected from a group consisting of a GvpA core sequence and a GvpB core sequence.

In various embodiments, wherein the first alpha helix comprises an amino acid sequence of SEQ ID NO: 12 or SEQ ID NO: 13, the first beta sheet comprises an amino acid sequence of SEQ ID NO: 14, SEQ ID NO: 15, SEQ ID NO: 16, SEQ ID NO: 17 or SEQ ID NO: 18, the second beta sheet comprises an amino acid sequence of SEQ ID NO: 19, SEQ ID NO: 20 or SEQ ID NO: 21, and the second alpha helix comprises an amino acid sequence of SEQ ID NO: 22, SEQ ID NO: 23 or SEQ ID NO: 24. Preferably, for SEQ ID NO: 22, SEQ ID NO: 23 or SEQ ID NO: 24, the X residue is Ala or Glu, and for SEQ ID NO: 22, SEQ ID NO: 23 or SEQ ID NO: 24, the Z residue is Val or Ile.

To be specific, the core sequence is a hydrophobic region of GvpA protein or GvpB protein. As illustrated in FIG. 4a, the core sequence is a tertiary protein structure consisting of 4 secondary protein structures arranged in a sequential manner: α-helix, β-sheet, β-sheet, α-helix. The GvpA protein or the GvpB protein is derived from cyanobacteria, halobacteria or soil bacteria. Preferably, the soil bacteria is *Priestia Megaterium*; the halobacteria is *Halobacterium salinarum*; the cyanobacteria is *Anabaena flos-aquae*.

In preferred embodiments, the GvpA protein has an amino acid sequence of SEQ ID NO: 1, and the GvpB protein has an amino acid sequence of SEQ ID NO: 2.

More specifically, the core sequence comprises $9^{th}$ amino acid (Serine) to the $61^{st}$ amino acid (Valine) of a GvpA protein or a GvpB protein from *P. megaterium* but not limited by this. In addition, all gas vesicle rib proteins carry the core sequence. Moreover, any homologs of GvpA protein or GvpB protein from cyanobacteria, halobacteria or soil bacteria, or any protein sequence homologous to the core sequence, can be genetically modified and play the role as the minor rib protein.

It should be noted that the secondary structures as mentioned above are predicted by Jpred 4, an online protein secondary structure prediction program. In FIG. 4a, regions forming α-helix are underlined and labelled as H, while regions forming β-sheet are labelled as S.

Illustrated in FIG. 4b is alignment of the minor rib protein with heterologous peptide, implying a schematic design of the minor rib protein, wherein the heterologous peptide is inserted at C-terminus of the core sequence, and for SEQ ID NO: 50 and SEQ ID NO: 51 in FIG. 4b, the X residues represent residues of the heterologous peptide sequence.

In other embodiments, the heterologous peptide is at least 6 amino acid long, and the heterologous peptide is derived from a human designed peptide sequence, a ligand, a hormone, a cytokine, a receptor, a paratope of antibody, a toxic protein, or a fluorescent protein.

In preferred embodiments, the major rib protein is a GvpB protein, and the minor rib protein is a core sequence with a heterologous peptide, wherein the heterologous peptide has at least 6 amino acids and is inserted in frame at C-terminus or at N-terminus of the core sequence.

Preferably, the core sequence comprises a truncated rib protein keeping the $1^{st}$ amino acid (Methionine) to the $61^{st}$ amino acid (Valine) of GvpA protein or GvpB protein from *P. megaterium*.

Exemplarily, the heterologous peptide of 6 to 56 amino acids or longer can be inserted at C-terminus of the core sequence, and the core sequence is a truncated form of the Gyp rib protein. The truncated Gyp rib protein and the heterologous peptide together forms the minor rib protein which carries a foreign peptide and results in a variety of applications in the biotech field. However, longer heterologous peptide leads to less stability of CGV and reduces the yield of CGV production.

In some embodiments, the heterologous peptide can be derived from two or more heterologous proteins as well. For example, 20-AA from protein A and 25-AA from protein B form a 45-AA heterologous peptide for the insertion to form the minor rib protein. Preferably, the heterologous peptides are derived from the protein sequence of pathogens, variable regions of antibodies, hormones, cytokines and ligands.

In various embodiments, the CGV is expressed in and purified from *E. coli*.

In one or various embodiments, the chimeric gas vesicle further comprises an assembly protein, and the assembly protein comprises a GvpP protein, a GvpQ protein or a combination thereof. The assembly protein is derived from *P. megaterium*. These proteins promote or accelerate or stabilize the formation of the CGV. The minor rib proteins are more evenly distributed on the CGV's surface with the presence of GvpP and GvpQ proteins. CGVs formed with the assistance of GvpP and GvpQ are more stable than CGVs without the assistance of GvpP and GvpQ.

In one particular embodiment, the GvpP protein has an amino acid sequence of SEQ ID NO: 3, and the GvpQ protein has an amino acid sequence of SEQ ID NO: 4.

In preferred embodiments, the CGV further comprises at least one accessory protein selected from a group consisting of a GvpR, a GvpN, a GvpF, a GvpG, a GvpL, a GvpS, a GvpK, a GvpJ, a GvpT and a GvpU.

By "chimeric gas vesicles (CGVs)" it means the gas vesicles which constitute with at least two kinds of Gyp rib proteins with different protein sequences. That is in contrast to all the gas vesicles described in previous publications which involve only one major rib protein, GvpA.

By "rib protein" it means the gas vesicle protein which forms the "rib" of GV and CGV. Once a gas vesicle forms, the rib protein can't be removed from a gas vesicle without the destruction of the gas vesicle. The gas vesicle rib protein(s) form ~4.6-nm 'ribs' that stack in array and run nearly perpendicular to the long axis of the gas vesicle and constitute the majority (97%) of the gas vesicle wall. The wall is 2-nm thick and consists of a single layer of the rib protein (FIG. 1). All gas vesicle rib protein has a hydrophobic tertiary structure including 4 secondary structures: α-helix, β-sheet, β-sheet and α-helix. The protein sequence of the tertiary structure is defined as "core sequence" (FIG. 4a, 4b).

By "major rib protein" it means the GvpA protein in cyanobacteria, halobacteria, and soil bacteria, and GvpB in *P. megaterium*, or any Gyp proteins homologous to and functionally equivalent to the GvpA protein, which forms the rib of the gas vesicle. The gas vesicle major rib protein is a rib protein with the "core sequence". Combining with a trace amount of Gyp accessory structure proteins (GvpF, GvpG, GvpJ, GvpK, GvpL, GvpS), it forms complete gas vesicles. It is sufficient to form gas vesicles without the involvement of other rib proteins. Once GV forms, the major rib protein cannot be removed from GV without GV destruction. The gas vesicle major rib protein constitutes 20 to 99.9% of total protein in the GV. It has been referred to as the major structure protein, the major constituent protein, the rib protein, etc.

By "minor rib protein" it means a rib protein with the "core sequence". It forms a complete gas vesicle only when another kind of rib protein is present. Most of the time the other kind of rib protein is a gas vesicle major rib protein, but it could be another gas vesicle minor rib protein with a different protein sequence. Once CGV forms, the minor rib protein cannot be removed from CGV without CGV destruction. The gas vesicle minor rib protein constitutes 3 to 80% of total protein in the CGV.

The native rib protein is a gas vesicle rib protein, GvpA or its homolog, found in nature. The truncated rib protein is a native gas vesicle rib protein with part of its amino acid sequence removed. The recombinant rib protein is a gas vesicle rib protein, either native or truncated, inserted in frame with a heterologous peptide at C-terminus, N-terminus or in the middle.

By "core sequence" it means the hydrophobic region of GvpA and its homologs which is a tertiary structure consisting of four secondary structures: α-helix, β-sheet, β-sheet, α-helix as indicated in FIGS. 4a to 4b. The "core sequence" spans from the $9^{th}$ amino acid (Serine) to the $61^{st}$ amino acid (Valine) of GvpA/B from *P. megaterium*. All gas vesicle rib proteins carry the core sequence.

In another aspect, the present invention discloses a protein expression system for expression of the chimeric gas vesicle, wherein the protein expression system comprises a first polynucleotide fragment encoding one of the Gyp rib proteins and a second polynucleotide fragment encoding the other one of the Gyp rib proteins. The protein expression system can be a DNA-based protein expression system or an RNA-based protein expression system.

In various embodiments, the first polynucleotide fragment encoding the major rib protein; and a second polynucleotide fragment encoding the minor rib protein, wherein the second polynucleotide fragment comprises a core polynucleotide encoding a core sequence; and a heterologous polynucleotide fragment encoding a heterologous peptide.

In preferred embodiments, the core sequence is characterized by a protein tertiary structure comprising a first alpha helix; a first beta sheet at C-terminus of the first alpha helix; a second beta sheet at C-terminus of the first beta sheet; and a second alpha helix at C-terminus of the second beta sheet.

Preferably, the core sequence is selected from a group consisting of a GvpA core sequence and a GvpB core sequence.

In particular, the core sequence is a hydrophobic region of GvpA protein or GvpB protein as illustrated in FIG. 4a, wherein the core sequence comprises $9^{th}$ to $61^{st}$ amino acid of a GvpA protein or a GvpB protein. Preferably, the core sequence is a tertiary protein structure consisting of 4 secondary protein structures arranged in a sequential manner: α-helix, β-sheet, β-sheet, α-helix, wherein the GvpA protein or the GvpB protein is derived from cyanobacteria, halobacteria or soil bacteria. Preferably, the soil bacteria is P. *Megaterium*; the halobacteria is *H. salinarum*; the cyanobacteria is *A. flos-aquae*.

In one preferred embodiment, the first polynucleotide fragment has a nucleotide sequence of SEQ ID NO: 5 or SEQ ID NO: 6.

In various embodiments, the heterologous peptide is at least 6 amino acids long, wherein the heterologous peptide is derived from a native protein sequence selected from a group consisting of a ligand, a hormone, a cytokine, a receptor, a paratope of antibody, a toxic protein and a fluorescent protein, or a human designed peptide sequence.

In some embodiments, the protein expression system further comprises an assembly polynucleotide fragment encoding an assembly protein, wherein the assembly protein comprises a GvpP protein, a GvpQ protein or a combination thereof. With presence of the assembly proteins, the minor rib proteins are more evenly distributed on the CGV's surface. While in absence of GvpP or GvpQ protein, CGVs demonstrate less stability and tend to assemble inappropriately or produce less amount than CGVs with the assistance of the assembly protein.

In certain embodiments, the assembly polynucleotide fragment is derived from *P. megaterium* gvpP, gvpQ or a combination thereof. Preferably, the assembly polynucleotide fragment has a nucleotide sequence of SEQ ID NO: 7, SEQ ID NO: 8 or SEQ ID NO: 9.

In some embodiments, the protein expression system further comprises an accessory polynucleotide fragment encoding at least one accessory protein, wherein the accessory protein is selected from a group consisting of a GvpR, a GvpN, a GvpF, a GvpG, a GvpL, a GvpS, a GvpK, a GvpJ, a GvpT and a GvpU. In certain embodiments, the accessory polynucleotide fragment is derived from *P. megaterium* gvpR, gvpN, gvpF, gvpG, gvpL, gvpS, gvpK, gvpJ, gvpT, gvpU or a combination thereof. Preferably, the accessory polynucleotide fragment has a nucleotide sequence of SEQ ID NO: 10.

In some embodiments, the protein expression system can be induced in a host to express the Gyp rib proteins, wherein the host comprises an archaeon cell, a prokaryotic cell, or a eukaryotic cell. Preferably, the archaeon cell is *H. salinarum*; the prokaryotic cell is *E. coli*; the eukaryotic cells are a mammalian cell, a yeast cell or an insect cell. More preferably, the host is *E. coli*.

Figure 8A:
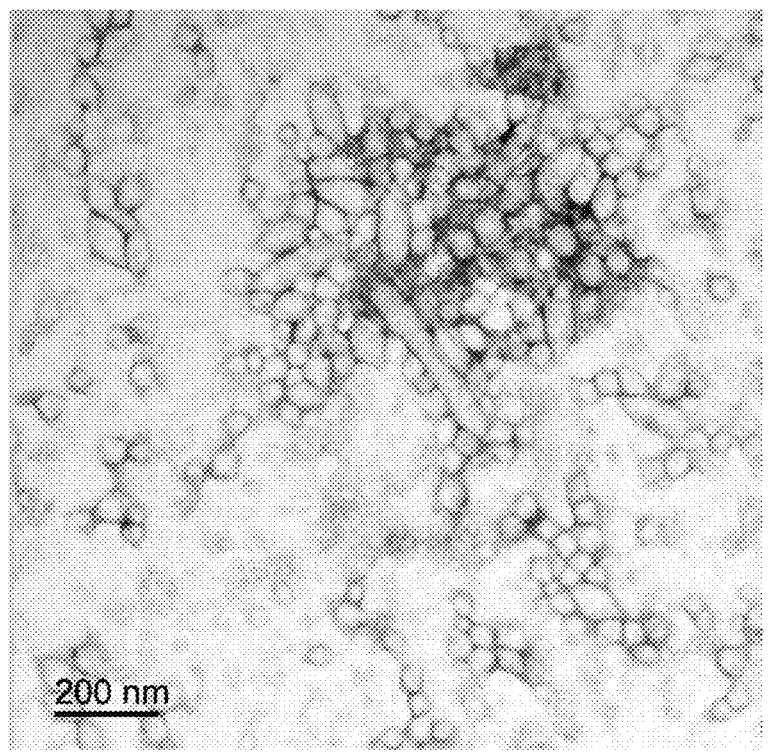
FIG. 8a is an electron microscopic graph of negative stained gas vesicles and the scale bar is equivalent to 200 nm.
Figure 8B:
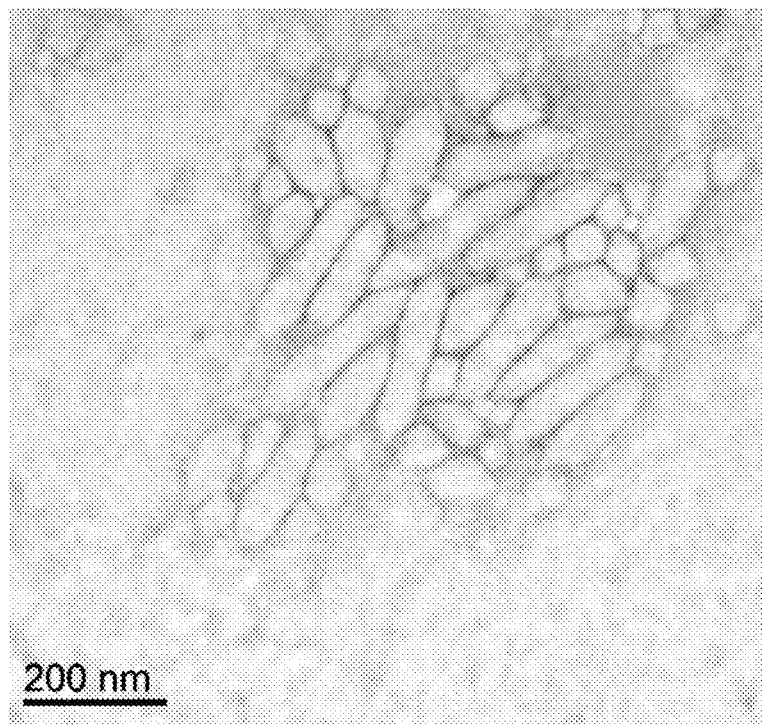
FIG. 8b is an electron microscopic graph of negative stained chimeric gas vesicles and the scale bar is equivalent to 200 nm.

As illustrated in FIG. 8a, the GVs purified from *E. coli* transformant with *P. megaterium* genes: gvpB (encoding a major rib protein) and gvpRNFGLSKJTU. The GVs are generally small (40×40 nm) with some large sized GV (40×200 nm). In an exemplary embodiment, as shown in FIG. 8b, the CGVs purified from *E. coli* transformant with *P. megaterium* genes: gvpA (encoding a recombinant minor rib protein), gvpPQ (assembly proteins), gvpB (encoding a major rib protein) and gvpRNFGLSKJTU. The CGVs are large in sizes (40×200 nm) in the presence of the two Gvp rib proteins and the assembly proteins. In the example as described above, the minor rib protein is a 77-AA truncated GvpA protein fused with a 17-AA heterologous peptide.

In some embodiments, to minimize the influence brought by longer heterologous peptide, numbers of amino acid deletion of the Gyp rib protein shall be considered. Without interruption of CGVs assembly and formation, a maximal deletion at GvpA C-terminus is 25-AA, while the maximal deletion at GvpB C-terminus is 27-AA. In an exemplary embodiment, maximal GvpA truncation and maximal heterologous peptide insertion were determined. As shown in TABLE 1, 25 amino acids can be removed from GvpA of *P. megaterium* without the destruction of CGV, and at least 56-AA heterologous peptide can be inserted into the truncated GvpA at C-terminus without the destruction of CGV. Besides, it can be inferred from TABLE 1 that less deletion of rib protein GvpA or GvpB at C-terminus is applicable when shorter heterologous peptide insertion is required.

TABLE 1

| Plasmid Name | C-terminus deletion (AA) | Heterologous peptide (AA) | Preserved GvpA C-terminus AA sequence | CGV production (µg/ml per culture) |
|---|---|---|---|---|
| pNL39 | 0 | 0 | WLRYAEAVGLLTD KVEEEGLPGRTEE RGAGLSF (SEQ ID NO: 25) | 10 |
| pNL114 | 6 | 0 | WLRYAEAVGLLTD KVEEEGLPGRTEE R (SEQ ID NO: 26) | 10 |
| pNL115 | 10 | 0 | WLRYAEAVGLLTD KVEEEGLPGR (SEQ ID NO: 27) | 10 |
| pNL119 | 13 | 0 | WLRYAEAVGLLTD KVEEEGL (SEQ ID NO: 28) | 10 |
| pNL118 | 16 | 0 | WLRYAEAVGLLTD KVEE (SEQ ID NO: 29) | 10 |
| pNL105 | 18 | 0 | WLRYAEAVGLLTD KV (SEQ ID NO: 30) | 10 |
| pNL106 | 19 | 0 | WLRYAEAVGLLTD K (SEQ ID NO: 31) | 10 |
| pNL107 | 20 | 0 | WLRYAEAVGLLTD (SEQ ID NO: 32) | 10 |
| pNL131 | 22 | 0 | WLRYAEAVGLL (SEQ ID NO: 33) | 10 |
| pNL132 | 24 | 0 | WLRYAEAVG (SEQ ID NO: 34) | 10 |
| pNL135 | 25 | 0 | WLRYAEAV (SEQ ID NO: 35) | 10 |

TABLE 1-continued

| Plasmid Name | C-terminus deletion (AA) | Heterologous peptide (AA) | Preserved GvpA C-terminus AA sequence | CGV production (µg/ml per culture) |
|---|---|---|---|---|
| pNL133 | 26 | 0 | WLRYAEA (SEQ ID NO: 36) | N/A |
| pNL136 | 27 | 0 | WLRYAE (SEQ ID NO: 37) | N/A |
| pNL134 | 28 | 0 | WLRYA (SEQ ID NO: 38) | N/A |
| pNL151 | 25 | 47 | WLRYAEAV + 47-AA (SEQ ID NO: 35) | 6 to 8 |
| pNL148 | 25 | 48 | WLRYAEAV + 48-AA (SEQ ID NO: 35) | 6 to 8 |
| pNL149 | 25 | 49 | WLRYAEAV + 49-AA (SEQ ID NO: 35) | 6 to 8 |
| pNL150 | 25 | 50 | WLRYAEAV + 50-AA (SEQ ID NO: 35) | 6 to 8 |
| pNL162 | 25 | 53 | WLRYAEAV + 53-AA (SEQ ID NO: 35) | 1 to 2 |
| pNL163 | 25 | 56 | WLRYAEAV + 56-AA (SEQ ID NO: 35) | 1 to 2 |

In some other embodiments, the protein expression system can be carried out by two or more different expression vectors for subsequent CGVs expression in a host. In one exemplary embodiment, a polynucleotide fragment encoding GvpA, GvpP and GvpQ is inserted in a first vector, and another polynucleotide fragment encoding GvpB, GvpR, GvpN, GvpF, GvpG, GvpL, GvpS, GvpK, GvpJ, GvpT and GvpU is inserted in a second vector. The first vector and the second vector are co-transformed into a host for production of the CGVs. Preferably, the vectors are derived from plasmid pST39 and plasmid pLysS for *E. coli* host.

By "vector" it means a nucleic acid molecule comprising gene-expressing elements and elements for genetic engineering so as to carry genes of interest into a selected host for specific biological functions such as protein expression or amplifying the copy number of genes of interest.

Figure 5:
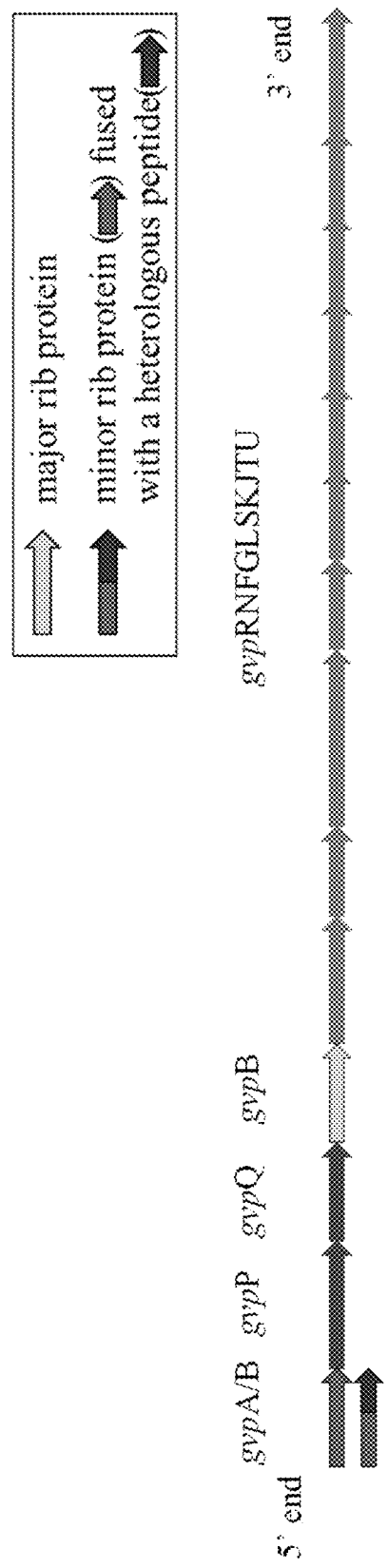
FIGS. 5 to 6 demonstrate genetic manipulation of gyp operons for CGV.

In other preferred embodiments, as illustrated in FIG. 5, to establish a gyp operon system comprising a single operon for protein expression of the CGVs, 3' end of the gvpAPQ polynucleotide fragment or the gypBPQ polynucleotide fragment is covalently linked to 5' end of the gypBRNFGL-SKJTU polynucleotide fragment so that a gvpAPQBRNFGLSKJTU polynucleotide fragment or a gypBPQBRNFGLSKJTU polynucleotide fragment is formed.

Figure 6:
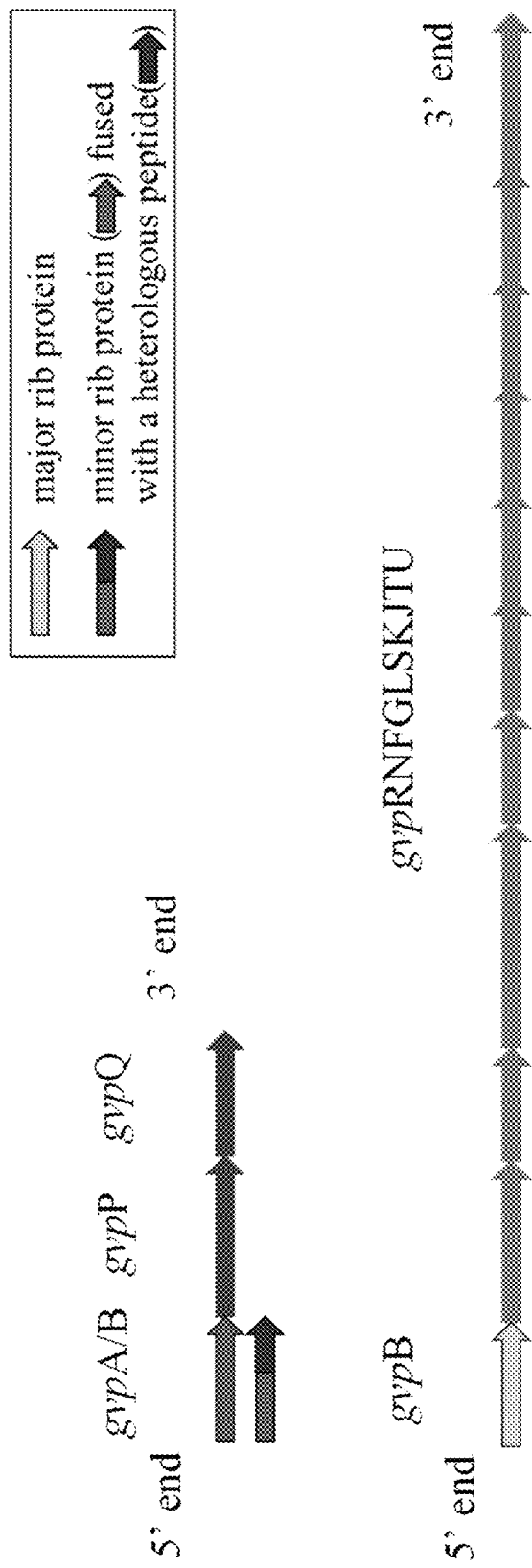

As illustrated in FIG. 6, to establish the gyp operon system comprising two operons for protein expression of the CGVs when the major rib protein and the minor rib protein are expressed separately, 3' end of the second polynucleotide fragment is covalently linked to 5' end of the assembly polynucleotide fragment so as to form a gvpAPQ polynucleotide fragment or a gvpBPQ polynucleotide fragment, while 3' end of the first polynucleotide fragment is covalently linked to 5' end of the accessory polynucleotide fragment so as to form a gvpARNFGLSKJTU polynucleotide fragment or a gvpBRNFGLSKJTU polynucleotide fragment.

Practically, an operator or a promoter is required upstream the gvpAPQ polynucleotide fragment, the gvpBPQ polynucleotide fragment, the gvpBRNFGLSKJTU polynucleotide fragment, the gvpAPQBRNFGLSKJTU polynucleotide fragment and the gypBPQBRNFGLSKJTU polynucleotide fragment so that the gyp operon system can be operated for synthesis of proteins required for CGV assembly upon induction of isopropylthiogalactoside (IPTG), lactose, methyl-β-D-thiogalactoside, phenyl-β-D-galactose or ortho-nitrophenyl-β-galactoside (ONPG), but not limited by this.

In one preferred embodiment, the gvpAPQBRNFGL-SKJTU polynucleotide fragment has a 7053-bp DNA sequence encoding GvpA, GvpP, GvpQ, GvpB, GvpR, GvpN, GvpF, GvpG, GvpL, GvpS, GvpK, GvpJ, GvpT and GvpU proteins and can be inserted into an appropriate expression vector for CGVs protein expression; preferably the gvpAPQBRNFGLSKJTU polynucleotide fragment has a nucleotide sequence of SEQ ID NO: 11.

In one another aspect, the present invention as shown in FIG. 9 discloses a method for producing the chimeric gas vesicles (CGVs) with a heterologous peptide fused with a genetically engineered gas vesicle minor rib protein GvpA or GvpB, the method comprises steps of:

(Step S1) Construction of plasmid: a plasmid is constructed by inserting a DNA sequence encoding a heterologous peptide having 6 to 56 amino acids or above in-frame at the C-terminus and/or N-terminus of the genetically engineered GvpA or GvpB protein in a recombinant gyp operon derived from *P. megaterium* by PCR and Gibson Assembly.

(Step S2) Transformation of plasmid: the constructed plasmid is transformed into *E. coli* or other suitable bacteria hosts capable of expression and production of CGV.

(Step S3) Induction: the transformant is grown in a proper environment to an optimal condition for inducing protein expression. The transformant is stimulated with IPTG (Isopropyl β-d-1-thiogalactopyranoside) or other inducers for the expression of the CGV.

(Step S4) Purification and quantification of the CGV.

To verify the sequence of the recombinant operon, the method further comprises a step of:

(Step S1.1) Sequence validation: The plasmid sequence with desired insertion is confirmed by DNA sequencing after step S1.

In some embodiments, the step S1 comprises constructing a CGV expression plasmid by inserting a DNA sequence encoding the minor rib protein into a gyp operon vector by PCR and Gibson Assembly, wherein the minor rib protein has a heterologous peptide at least 6 amino acids (AAs) inserted in frame as a recombinant.

In yet one another aspect, the present invention as shown in FIG. 10 discloses a method for eliciting immune response by administrating CGV-Covid-19 to a subject in need, the method comprising steps of:

(Step A) Purification and quantification of CGV-Covid-19 vaccine in PBS.

(Step B) Administration of the CGV-Covid-19 vaccine into the subject in need.

(Step C) Detection of the immune responses on the subject.

In a certain embodiment, CGV-Covid-19 is administrated on the subject in need via intranasal administration, wherein a 17-AA heterologous peptide derived from S-protein of Covid-19 virus is inserted at C-terminus of the core sequence so that the CGV presents an epitope derived from SARS-CoV-2 (Covid-19) spike protein. Enzyme-linked immunosorbent assay (ELISA) is applied to measure elicitation of the immune responses by the CGV-Covid-19 vaccine, but the measure for detection is not limited by this. The subject in need includes human, mice, canine, porcine, chimpanzee or other mammal.

The CGVs of the invention may be used as vaccines for infectious diseases, therapeutic vaccines for cancer and other diseases. They can be therapeutic agents (such as carrying hormones, cytokines, ligands, or part of variable regions of antibodies) for cancer, metabolic diseases, and other diseases. They can also function as non-invasive contrast agents for ultrasound, MRI and other imaging technologies. In short, a wide variety of applications are possible with the CGVs used as a nanoparticle.

Example 1

Construction and Confirmation of Plasmid

Any effective *E. coli* plasmid/host expression system can be used, such as pBB322 derived plasmids/BL21 *E. coli* strain (New England Biolab), pET28 plasmid/BL21(A1) *E. coli* strain (Thermo Fisher) or pST39 plasmid/Rosetta *E. coli* strain (Millipore Sigma).

The plasmid was digested with restriction enzyme/enzymes or PCR with particular primers to generate the corresponding DNA fragment. The proper DNA primers encoding a peptide of interest were designed and ordered from any commercial primer vendors by one of ordinary skill in the art.

The DNA fragment encoding heterologous truncated GvpA protein or GvpB protein with a peptide of interest, and a DNA fragment carrying the rest of 13 gyp genes: gvpPQBRNFGLSKJTU from *P. megaterium* were amplified by PCR with the proper DNA primers. The fragments were subsequently ligated by Gibson Assembly (Thermo Fisher). The Gibson Assembly mixture was transformed into proper *E. coli* competent cells and transformants were analyzed and sequenced by one of ordinary skill in the art.

Expression and Production of CGV

The plasmids with the correct DNA sequence insertion were transformed into desired *E. coli* hosts. A single colony was picked and inoculated with LB media with appropriate selection antibiotics. CGV expression can be induced by IPTG or other inducers and purification is done by a modified protocol. The protocol including following steps:

a. Transformed *E. coli* were cultured for 20 to 22 hours and then centrifuged at 500 g for 1 to 2 hours.
b. The pellet was resuspended in PBS buffer and lysed by detergent, lysozyme and DNase.
c. The cell lysate was centrifuged at 500 g for 5 to 30 minutes so that CGV was isolated from cell debris. Of note, the CGV floated at the top of the lysate suspension.
d. The cell debris and the midnatant were removed by a needle.
e. The remaining CGV was suspended in PBS.
f. Step c to Step e were repeated for 10 times and 99% purity of CGV was obtained.
g. Final concentration of CGV was measured by a spectrophotometer at $OD_{500}$ (NanoDrop ND-1000, Thermo Scientific). Of note, one $OD_{500}$ of CGV is equivalent to 145 µg/ml of protein.

Example 2

To verify that insertion of heterologous peptide from one foreign protein or more foreign proteins can be realized in the present invention, in example 2, one 20-AA peptide from H1N1 virus HA (hemagglutinin) protein and another 20-AA peptide from Covid-19 virus Spike protein were linked to form a 40-AA insertion peptide. Then, the minor rib genes with heterologous peptide from two foreign proteins were inserted into the 14 gene gyp operon on the same plasmid or on two individual plasmid vectors. Transformation or co-transformation of the plasmid(s) into *E. coli* competent cells such that CGV particles carrying two or more heterologous peptides were brought on mass production.

Example 3

To further validate protein expression of CGVs carrying various heterologous peptides, CGVs produced and isolated by procedures as described in example 1 were confirmed by Western Dot Blot.

TABLE 2

| Dot | CGV samples | Heterologous Peptide Sequences | S-Protein Sequence |
| --- | --- | --- | --- |
| 1 | Positive control | Covid-19 S-protein | S-Protein |
| 2 | pNL39 | GvpA without insertion of heterogeneous sequence | No heterogeneous peptide sequence |
| 3 | pNL66 | TGCVIAW NSNNLDS (SEQ ID NO: 39) | T430 to S443 |
| 4 | pNL67 | NLDSKVG GNYNYLY (SEQ ID NO: 40) | N440 to Y453 |
| 5 | pNL68 | NYLYRLF RKSNLKP (SEQ ID NO: 41) | N450 to P463 |
| 6 | pNL69 | NLKPFER DISTEIY (SEQ ID NO: 42) | N460 to Y473 |
| 7 | pNL70 | TEIYQAG STPCNGV (SEQ ID NO: 43) | T470 to V483 |
| 8 | pNL71 | CNGVEGF NCYFPLQ (SEQ ID NO: 44) | C480 to Q493 |
| 9 | pNL72 | FPLQSYG FQPTNGV (SEQ ID NO: 45) | F490 to V503 |
| 10 | pNL73 | TNGVGYQ PYRVVVL (SEQ ID NO: 46) | T500 to S513 |

CGV samples with various heterologous peptides were purified from the *E. coli* culture transformed with the corresponding plasmid constructs. The Western Dot Blot was done with rabbit anti-Covid-19 S protein as the primary antibody and goat anti-rabbit IgG-HRP as secondary antibody.

Figure 7:
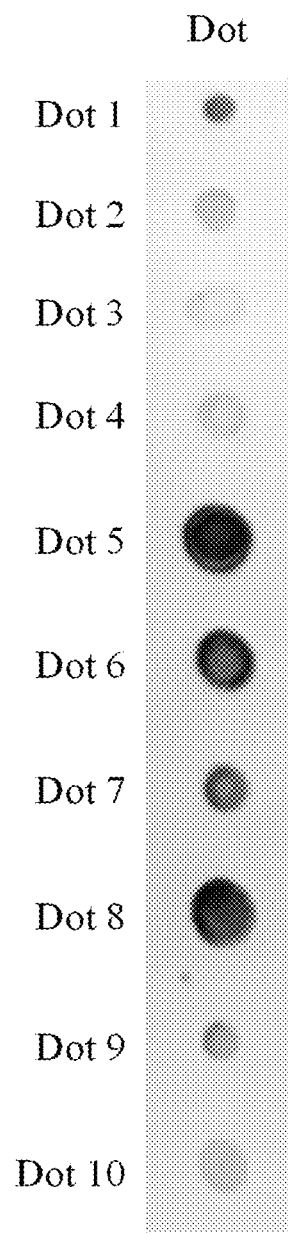
FIG. 7 demonstrates Western Dot Blot for confirmation of CGVs carrying various heterologous.

As shown in FIG. 7, dots representing positive CGVs were Dot 5 to 8, which suggests that antigen region of Covid-19 S-protein is between $450^{th}$ to $493^{rd}$ AA. In TABLE 2, detailed information of Covid-19 S protein sequences serving as inserts in recombinant gvp operons were listed down, and antigen regions of Covid-19 S protein were identified as SEQ ID NO: 41 (N450 to P463), SEQ ID NO: 42 (N460 to Y473), SEQ ID NO: 43 (T470 to V483) and SEQ ID NO: 44 (C480 to Q493), respectively.

The advantages of the present invention, chimeric gas vesicles (CGVs), over traditional GV and GVNP are numerous.

For example, previous attempts of direct genetic modification of GvpA in the conventional GV are unsuccessful due to the rigidity of GvpA in the GV. To date, no more than 5-AA heterologous peptide can be inserted at the C-terminus of GvpA without the destruction of GV. The CGV disclosed in the present invention overcomes this stability limitation and makes the CGVs possible for various applications. In GV research in halobacteria, the genetically modified GvpC of GVNP attaches to GV via protein-protein interaction, and is vulnerable to thermohaline fluctuations. This makes the GvpC easy to fall off from the GVNP, thus greatly reduces the possibility of using the conventional GVs for applications. In the CGVs, the heterologous peptide can be inserted or fused covalently with the truncated/native GvpA or its homolog to form the rib protein. As a part of the rib structure, the fall-off problem of the heterologous peptide present in the conventional GVs is eliminated. For industrial or commercial productions, the making of the CGVs can be accomplished in much shorter production cycle. In some instances, it can be produced within 2 days, which is drastically shorter than the production cycle of GVNPs in halobacteria or GVs in cyanobacteria. The CGVs are more stable than the conventional GVs. The CGVs produced in *E. coli* with gyp operon from *P. megaterium* are more stable than any other GVs previously known. The CGVs of the present invention have a higher "critical collapse pressure" than the conventional GVs. For storage, the CGVs in one of the embodiments maintain their integrity at room temperature for at least one month, and at 4° C. for at least six months, without any degradation. All these features of the CGVs of the present invention increases immensely the possibilities of its applications in the future.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

What is claimed is:

1. A chimeric gas vesicle (CGV) comprising at least two Gyp rib proteins, wherein the at least two Gyp rib proteins comprises:
   a major rib protein comprising a GvpB protein deriving from *P. megaterium*;
   a minor rib protein comprising a core sequence comprising the 9th to 61st amino acid residues of SEQ ID NO:1, where the amino acid sequence of SEQ ID NO: 1 is a protein derived from *P. megaterium*; and
   a heterologous peptide of 6 to 56 amino acids in frame at C-terminus or N-terminus of the core sequence.

2. The chimeric gas vesicle as claimed in claim 1, wherein the heterologous peptide is derived from a native peptide sequence selected from the group consisting of a ligand, a hormone, a cytokine, a receptor, a paratope of an antibody, a toxic protein, a fluorescent protein, and a synthetic peptide sequence.

3. The chimeric gas vesicle as claimed in claim 1, wherein expression and purification of the CGV proceed in *E. coli*.

4. The chimeric gas vesicle as claimed in claim 1, wherein the CGV assembles with assistance of at least one assembly protein, wherein the assembly protein comprises a GvpP protein, a GvpQ protein or a combination thereof.

5. The chimeric gas vesicle as claimed in claim 1, wherein the major rib protein and the minor rib protein form at least 90% of the chimeric gas vesicle by dry weight.

* * * * *

```
                            SEQUENCE LISTING

<160> NUMBER OF SEQ ID NOS: 51

<210> SEQ ID NO 1
<211> LENGTH: 86
<212> TYPE: PRT
<213> ORGANISM: Priestia megaterium
<220> FEATURE:
<221> NAME/KEY: GvpA
<222> LOCATION: (1)..(86)

<400> SEQUENCE: 1

Met Ser Ile Gln Lys Ser Thr Asp Ser Ser Leu Ala Glu Val Ile
1               5                   10                  15

Asp Arg Ile Leu Asp Lys Gly Ile Val Ile Asp Ala Phe Ala Arg Val
                20                  25                  30

Ser Leu Val Gly Ile Glu Ile Leu Thr Ile Glu Ala Arg Val Val Ile
            35                  40                  45

Ala Ser Val Asp Thr Trp Leu Arg Tyr Ala Glu Ala Val Gly Leu Leu
        50                  55                  60

Thr Asp Lys Val Glu Glu Gly Leu Pro Gly Arg Thr Glu Arg
65                  70                  75                  80

Gly Ala Gly Leu Ser Phe
                85

<210> SEQ ID NO 2
<211> LENGTH: 88
<212> TYPE: PRT
<213> ORGANISM: Priestia megaterium
<220> FEATURE:
<221> NAME/KEY: GvpB
<222> LOCATION: (1)..(88)

<400> SEQUENCE: 2

Met Ser Ile Gln Lys Ser Thr Asn Ser Ser Leu Ala Glu Val Ile
1               5                   10                  15

Asp Arg Ile Leu Asp Lys Gly Ile Val Ile Asp Ala Phe Ala Arg Val
                20                  25                  30

Ser Val Val Gly Ile Glu Ile Leu Thr Ile Glu Ala Arg Val Val Ile
            35                  40                  45

Ala Ser Val Asp Thr Trp Leu Arg Tyr Ala Glu Ala Val Gly Leu Leu
        50                  55                  60

Arg Asp Asp Val Glu Glu Asn Gly Leu Pro Glu Arg Ser Asn Ser Ser
65                  70                  75                  80

Glu Gly Gln Pro Arg Phe Ser Ile
                85

<210> SEQ ID NO 3
<211> LENGTH: 161
<212> TYPE: PRT
<213> ORGANISM: Priestia megaterium
<220> FEATURE:
<221> NAME/KEY: GvpP
<222> LOCATION: (1)..(161)

<400> SEQUENCE: 3

Met Ser Thr Thr Asp Asn Asn Met Gln Ser Glu Lys Gln Glu Asn
1               5                   10                  15
```

-continued

Gln Gln Glu Glu Lys Thr Gln Asn Ser Leu Asn Leu Ala Ile Leu Gly
           20                  25                  30

Gly Val Val Gly Ala Gly Ile Gly Leu Leu Ser Ser Pro Gln Thr Ser
       35                  40                  45

Lys Lys Val Leu Ser Arg Leu Gly Gln Ser Glu Ile Val Arg Ala Thr
50                  55                  60

Gly Gln Glu Leu Arg Arg Asn Ala Gln Asp Ile Leu Thr Gln Gln Ala
65                  70                  75                  80

Met Gly Ala Leu Arg Gln Thr Ala Thr Gly Tyr Leu Glu Lys Asp Asn
               85                  90                  95

Leu Ser Lys Leu Leu Ala Pro Lys Lys Lys Asp Asp Ala Ser Asn
              100                 105                 110

Glu Gln Gly Asp Ser Gln Glu Val Ser Gln Ser Ala Glu Met Glu
              115                 120                 125

Thr Ser Gln Tyr Glu Glu Leu Lys Glu Glu Asn Lys Asn Met Asn Asp
              130                 135                 140

Gln Leu Gln Arg Ile Glu Glu Met Leu Asn Lys Leu Met Asp Ala Lys
145                 150                 155                 160

Lys

<210> SEQ ID NO 4
<211> LENGTH: 157
<212> TYPE: PRT
<213> ORGANISM: Priestia megaterium
<220> FEATURE:
<221> NAME/KEY: GvpQ
<222> LOCATION: (1)..(157)

<400> SEQUENCE: 4

Met Asp Lys Lys Asp Val Glu Lys Ala Ala Leu Lys Ala Gly Lys Lys
1               5                   10                  15

Ile Ile Asp His Thr Pro Glu Pro Val Lys Glu Lys Ile Glu Glu Lys
               20                  25                  30

Val Lys Glu Lys Ala Lys Glu Lys Phe Val Glu Lys Thr Glu Gly Lys
           35                  40                  45

Leu Gln Glu Lys Ala Asn Glu Ala Ser Glu Lys Leu Gln Glu Thr Lys
       50                  55                  60

Glu Lys Asn Ala Gln Lys Val His Gly Lys Gly Glu Asp Ala Lys Glu
65                  70                  75                  80

Lys Leu Gln Asp Val Leu Leu Ser Val Lys Asp Lys Leu Ser Asp Val
               85                  90                  95

Lys Glu Ala Gly Glu Asn Phe Gln Glu Lys Val Ser Ser Ser Asp Asp
              100                 105                 110

Lys Glu Lys Ser Lys Asn Lys Arg Lys Ile Lys Gly Val Asn Gln Ile
              115                 120                 125

Lys Lys Ala Thr Asp Ile Lys Ser Ser Thr Lys Ile Lys Ser Ser Asn
130                 135                 140

Asp Ile Lys Ser Ser Thr Asp Leu Lys Thr Met Gly Ser
145                 150                 155

<210> SEQ ID NO 5
<211> LENGTH: 258
<212> TYPE: DNA
<213> ORGANISM: Priestia megaterium
<220> FEATURE:
<221> NAME/KEY: gvpA
<222> LOCATION: (1)..(258)

```
<400> SEQUENCE: 5
atgagtattc aaaaaagtac agatagttct agtttagcag aagtgattga tcgaattctc    60
gacaaaggga ttgtcatcga tgcttttgcc cgagtatcac tcgtaggaat tgaaatttta   120
acgattgaag cacgagtcgt tattgcaagt gtcgatacgt ggcttcgcta cgcagaagcc   180
gttgggttat taaccgacaa agtagaggaa gaagggctgc ctggccgaac agaggagcga   240
ggagcagggc ttagcttt                                                 258

<210> SEQ ID NO 6
<211> LENGTH: 264
<212> TYPE: DNA
<213> ORGANISM: Priestia megaterium
<220> FEATURE:
<221> NAME/KEY: gvpB
<222> LOCATION: (1)..(264)

<400> SEQUENCE: 6
atgtctattc aaaaaagtac taatagttca agtttagcag aagtcattga ccgtatttta    60
gataaaggaa ttgttattga tgcttttgca agagtttctg ttgtaggaat tgaaatttta   120
acgattgaag cgcgagtggt tattgccagt gttgatacat ggttacgcta tgcagaagca   180
gtagggcttc ttcgtgacga cgtagaagaa aacggtcttc ctgaacgttc aaattcaagt   240
gaagggcagc cgcgttttag tatt                                          264

<210> SEQ ID NO 7
<211> LENGTH: 483
<212> TYPE: DNA
<213> ORGANISM: Priestia megaterium
<220> FEATURE:
<221> NAME/KEY: gvpP
<222> LOCATION: (1)..(483)

<400> SEQUENCE: 7
atgtcaacaa ctgataacaa tatgcaaagt gaaaaacaag aaaatcagca gcaggaagaa    60
aaaacgcaaa actctttaaa tcttgctatt ttaggaggcg tagtaggagc gggaattgga   120
cttctttcaa gtcctcaaac gagtaaaaaa gtactcagcc gcttaggaca atcagaaatt   180
gtacgtgcga caggacaaga gttaagaaga aacgcacagg atattctaac gcagcaagcg   240
atgggagcat taaggcagac ggctacagga tatcttgaaa aagacaattt aagcaagctg   300
ctggcaccta aaagaaaaa agatgatgca tcaaatgaac agggcgattc gcaggaagaa   360
gtcagccaaa gcgcagaaat ggaaacgtct cagtacgaag agctaaaaga agaaaataaa   420
aatatgaacg accagctgca gcgcattgaa gagatgctaa acaaactcat ggacgcgaag   480
aag                                                                 483

<210> SEQ ID NO 8
<211> LENGTH: 471
<212> TYPE: DNA
<213> ORGANISM: Priestia megaterium
<220> FEATURE:
<221> NAME/KEY: gvpQ
<222> LOCATION: (1)..(471)

<400> SEQUENCE: 8
atggataaaa aagatgtgga gaaagcagcc ttaaaagcag gaaaaaagat catcgatcat    60
acgcctgaac tgttaagga aaagataga gaaaaggtta agaaaaaagc gaaagaaaaa   120
tttgtcgaaa aaactgaagg gaaactgcag gaaaaagcaa atgaagcgtc agaaaaactg   180
```

| | |
|---|---|
| caggaaacaa aagaaaaaaa tgcccaaaag gtacacggca aaggggaaga cgcaaaagaa | 240 |
| aagctccaag acgtcttact atcagtaaaa gataagctta gcgatgtgaa agaagctgga | 300 |
| gaaaactttc aagaaaaagt ttcttcttca gacgataaag agaagtcaaa aaataagcgg | 360 |
| aaaataaaag gcgtaaatca gattaaaaaa gcaacggata ttaaaagctc tactaagatt | 420 |
| aaaagttcta atgatattaa atcatctaca gatttaaaaa caatgggatc a | 471 |

<210> SEQ ID NO 9
<211> LENGTH: 985
<212> TYPE: DNA
<213> ORGANISM: Priestia megaterium
<220> FEATURE:
<221> NAME/KEY: gvpP
<222> LOCATION: (1)..(483)
<220> FEATURE:
<221> NAME/KEY: gvpQ
<222> LOCATION: (572)..(982)

<400> SEQUENCE: 9

| | |
|---|---|
| atgtcaacaa ctgataacaa tatgcaaagt gaaaaacaag aaaatcagca gcaggaagaa | 60 |
| aaaacgcaaa actcttttaaa tcttgctatt ttaggaggcg tagtaggagc gggaattgga | 120 |
| cttcttttcaa gtcctcaaac gagtaaaaaa gtactcagcc gcttaggaca atcagaaatt | 180 |
| gtacgtgcga caggacaaga gttaagaaga aacgcacagg atattctaac gcagcaagcg | 240 |
| atgggagcat taaggcagac ggctacagga tatcttgaaa aagacaattt aagcaagctg | 300 |
| ctggcaccta aaagaaaaa agatgatgca tcaaatgaac agggcgattc gcaggaagaa | 360 |
| gtcagccaaa gcgcagaaat ggaaacgtct cagtacgaag agctaaaaga agaaaataaa | 420 |
| aatatgaacg accagctgca gcgcattgaa gagatgctaa acaaactcat ggacgcgaag | 480 |
| aagtaagata tccgtcctga aggggaattt catggataaa aaagatgtgg agaaagcagc | 540 |
| cttaaaagca ggaaaaaaga tcatcgatca tacgcctgaa cctgttaagg aaaagataga | 600 |
| agaaaaggtt aaagaaaaag cgaaagaaaa atttgtcgaa aaaactgaag ggaaactgca | 660 |
| ggaaaaagca aatgaagcgt cagaaaaact gcaggaaaca aagaaaaaaa atgcccaaaa | 720 |
| ggtacacggc aaaggggaag acgcaaaaga aaagctccaa gacgtcttac tatcagtaaa | 780 |
| agataagctt agcgatgtga aagaagctgg agaaaacttt caagaaaaag tttcttcttc | 840 |
| agacgataaa gagaagtcaa aaataagcg gaaaataaaa ggcgtaaatc agattaaaaa | 900 |
| agcaacggat attaaaagct ctactaagat taaaagttct aatgatatta aatcatctac | 960 |
| agatttaaaa acaatgggat cataa | 985 |

<210> SEQ ID NO 10
<211> LENGTH: 5434
<212> TYPE: DNA
<213> ORGANISM: Priestia megaterium
<220> FEATURE:
<221> NAME/KEY: gvpRNFGLSKJTU
<222> LOCATION: (1)..(5434)

<400> SEQUENCE: 10

| | |
|---|---|
| tatgaagtgg tatggaacct tccttttttg agggtggttc cagcttttag atctaactat | 60 |
| tggaggctac taaaaatgga aattaaaaaa attatgcaag ccgtgaacga cttttttcggt | 120 |
| gaacacgtag ctcctcctca taaaattacc tcggtggaag ctactgaaga tgaaggttgg | 180 |
| agagttattg ttgaagtcat tgaagaacga gaatatatga aaaaatacgc caaagatgaa | 240 |
| atgctcggaa cgtacgagtg ctttgtaaat aaagaaaaag aagtcatttc attcaaacga | 300 |

```
ctcgacgtca gatatagaag cgccattggc attgaagcat aaacgataag atggcaggag      360
gaacgtaaaa atgaccgtct taacagacaa aaggaaaaaa ggcagtggag cttttataca      420
agatgacgag accaaagagg ttctttcaag agcgctgagc tatttaaaat ccggctattc      480
cattcatttt acaggtcctg ccggcggagg caaaacctct ttagcgcgag cgcttgctaa      540
aaagagaaag cgtcctgtaa tgctgatgca cgggaatcac gagctcaaca acaaagattt      600
aattggcgat tttacgggat acacgagcaa aaagtaatc gaccagtacg ttcgttctgt       660
ctataaaaaa gatgaacagg tgagtgaaaa ctggcaggat ggccgattgc ttgaagctgt      720
aaaaaatggc tatacgctga tttacgacga atttactcgt tctaagcctg cgacgaataa      780
tatctttcta tcgatattag aagaaggcgt gctgccgctg tatggagtaa aaatgaccga     840
tccttttgtg cgcgtgcatc ccgatttccg cgtcatcttc acaagcaatc cagctgagta     900
tgccggcgta tatgatacgc aagatgcgct tctcgacagg ttaattacca tgtttattga    960
ttataaagac atcgacagag agacagcgat tttaacggag aaaacggacg tagaagaaga   1020
tgaagcgcgc acaattgtaa cgctcgtagc aaacgtgcga aaccgctctg agacgaaaa    1080 cagcagcgga cttagcctgc gggcttcgct tatgatcgct acccttgcca cgcagcaaga   1140
cattcctatc gatggaagtg acgaagattt tcaaacgtta tgtatcgata ttttgcatca   1200
tccgcttacc aaatgtttgg atgaagaaaa tgcaaaaagc aaagccgaaa aaatcatttt   1260
agaagaatgt aagaatatag acactgaaga aaagtaaagg agcttgaaaa catgagtgaa   1320
acaaacgaaa caggtatttta tatttttagc gccattcaaa cggataaaga cgaagaattt   1380
ggcgccgtgg aagtagaagg aacaaaagct gaaacatttt tgattcgcta caagacgcg     1440 gctatggtag cagctgaagt accgatgaaa atttatcatc ctaatcgcca aaatttatta    1500
atgcatcaaa acgcagtagc agcgattatg gacaagaacg atacggttat tccaatcagc   1560
tttgggaatg tattcaaatc aaaagaagac gtaaaagttc ttttggaaaa cctttatccg   1620
cagtttgaaa agctgttttcc agcgatcaaa ggaaaaattg aagtcggttt aaaagtaatt   1680
gggaaaaaag aatggcttga gaaaaaagta acgaaaaatc ctgaacttga aaagtatca    1740 gcatccgtaa aaggaaaatc agaagcagcc ggttattatg agcgtattca acttggagga   1800
atggctcaaa agatgtttac ttccctgcaa aaagaagtca agacagatgt gttttctccg   1860
cttgaagaag cagcggaagc agcaaaagca aatgagccaa cgggcgaaac gatgctttta   1920
aacgcgtctt tcttaattaa ccgagaagat gaagcgaagt ttgatgaaaa agtaaatgaa   1980
gcgcatgaaa actggaaaga caaagccgat tttcattaca gcggtccttg gcctgcttat   2040
aattttgtga acattcgcct aaaagtagaa gagaaataac gtgcttcaca aattagtaac   2100
cgcacccatt aaccttgtag tgaaaatcgg cgaaaaagta caggaagaag ctgataaaca   2160
gctatatgac cttccgacga ttcagcaaaa gctcattcag cttcaaatga tgtttgagct   2220
tggtgaaatt ccagaagaag cgtttcaaga aaagaagat gaattgttaa tgaggtacga    2280
aattgcgaaa cgcagagaaa ttgaacaatg ggaagagcta acacaaaaaa gaaatgagga   2340
atcctagatg ggagaattac tgtatttata cggtttaatt ccaacaaaag aagcagcagc   2400
catagagccg tttccatttt ataagggggtt tgacggagaa cattcactgt acccaattgc   2460
gtttgatcag gtgacggctg tagttttttaa gctggatgct gacacctatt cagaaaaagt   2520
gattcaagaa aaaatggagc aggatatgag ctggctgcag gaaaaagcat tcatcatca   2580 cgaaacggta gccgctttgt acgaagaatt tacgatcatt ccattaaaat tttgcaccat   2640
ttataaaggt gaagaaagtc tgcaggcagc tattgagatt aacaaagaaa agatagagaa   2700
```

```
ttcactgacg ctgcttcaag gaaatgaaga gtggaatgtg aaaatttact gtgatgatac    2760
agagcttaaa aaaggaatca gcgaaacgaa tgaaagcgtg aaagcgaaaa aacaagaaat    2820
tagtcactta tcaccaggaa gacagttttt tgaaaagaaa aaaatagatc agctgattga    2880
aaaagaatta gagcttcaca aaaacaaagt gtgtgaagag atacatgaca agctaataga    2940
attatcgctt tatgactctg ttaaaaagaa ttggagcaaa gacgtaactg gcgcagctga    3000
acagatggcg tggaacagcg tgtttcttct cccgtctctg cagattacta agttcgtaaa    3060
cgaaatagaa gagcttcagc aaaggcttga aaataaaggc tggaagtttg aagtgacggg    3120
accatggccg ccctatcatt tctcgagctt tgcgtaaagt gaggaattaa cattatgtct    3180
cttaaacaat ccatggagaa taaagatatt gctcttattg atattttaga tgtcatttta    3240
gataaaggag tcgccattaa aggagactta atcatttcca tagctggcgt cgatttagtg    3300
tatttggatt tgcgggtgct tatttcttcg gttgaaacgc ttgtgcaagc aaaagaagga    3360
aatcacaaac caatcacttc tgaacaattt gataaacaaa aggaggaatt aatggatgca    3420
accggtcagc caagcaaatg gacgaatcca cttggatcct gatcaagctg aacaaggctt    3480
agcgcagctt gtgatgacag ttattgagct attgaggcaa atcgttgaac gtcatgccat    3540
gaggcgggtg gagggtggaa cgttgacgga cgaacaaatt gaaaacttag gaattgcact    3600
aatgaactta aagaaaaaaa tggacgagtt gaaagaggtg ttcggtctgg atgcagaaga    3660
tttaaatatt gatcttggac cgctaggcag cctgctttaa gcggtcagta ggaggaacag    3720
tatggcagtc gaacataata tgcagtcaag tacgattgta gatgtgctcg aaaagatttt    3780
ggataaagga gtcgttatag cgggggacat caccgtagga attgcagatg tcgagctatt    3840
aacgattaag atccgcttga ttgtggcttc ggttgataag gcaaaagaaa tcggcatgga    3900
ctggtgggaa aatgatccgt atctcagttc aaaaggagcc aataacaaag cgctcgaaga    3960
agaaaataaa atgctgcatg agcggttaaa aacgcttgaa gaaaaaatag aaacgaaacg    4020
ttaaaaactg tacgctactt aaaaaatgga gggatttaca atggcaactg aaacaaaatt    4080
agataacaca caggcagaaa acaaggaaaa taaaaatgcg gaaaacggtt caaaagaaaa    4140
gaacggttca aaagcaagca aaacaacaag cagcgggcca atcaaacgag cggtagcagg    4200
aggcatcatc ggtgcaacga ttggatatgt atcgactcct gaaaatcgaa aaagtctcct    4260
tgaccgcatt gatacagacg aattaaaaag caaagcatct gatttaggaa caaaggtaaa    4320
agaaaaatca aaagcagcg tggccagcct gaaaacatct gcgggaagct tgtttaaaaa    4380
agatgaagat aaatcaaaag atgatgaaga aacgtaaat tcttctagta gcgaaacaga    4440
agacgatgac gttcaagagt acgacgagtt aaaagaagaa aatcaaactc ttcaagatcg    4500
cttatcacag cttgaagaaa aaatgaacat gcttgttgag cttagcctca ataaaaatca    4560
agacgaagaa gcggaagata cagattccga cgaagaagag aacgatgaga acgatgaaaa    4620
cgatgaaaac gagcaggacg atgaaaacga agaagaaaca tctaagccac gtaaaaagga    4680
taaaaaagaa gctgaggaag aagaaagtga aagtgacgaa gacagcgagg aagaagagga    4740
agattctcgc tcaaacaaaa aaaataaaaa agtaaaaaca gaagaagaag acgaagatga    4800
aagcgaagaa gaaaaaaagg aagcgaaacc aaaaaagtca acagctaaaa aatcaaaaaa    4860
tacaaaagca aagaaaaaca cggacgaaga agatgatgaa gcaacatctc tttctagtga    4920
agacgataca acagcctaag acgtaaagga ggaagaaag acatgagtac aggcccttct    4980
ttttcaacta aagacaatac gcttgaatac tttgtgaaag cttctaataa acacggcttt    5040
```

```
tcacttgata tttcattaaa tgtaaacggc gctgtgattt ccggtaccat gatttcagca    5100
aaagaatact ttgattactt aagcgaaacg tttgaagaag gcagtgaagt ggctcaggcg    5160
ctaagcgaac aattctcttt agcaagcgaa gcgagcgaat caaacggaga agcagaagcc    5220
cattttattc atttgaaaaa tacaaagatt tactgtggag acagtaaatc tactccttct    5280
aaaggcaaaa tcttttggag agggaaaata gcagaagtag acgggttttt cttaggaaag    5340
atttctgatg caaaatcaac gagtaaaaag agttcataaa aaacggcggg gtgattgccc    5400
cgccgttttt tagtgatgtg atgagatgtg cagc                               5434
```

<210> SEQ ID NO 11
<211> LENGTH: 7053
<212> TYPE: DNA
<213> ORGANISM: Priestia megaterium
<220> FEATURE:
<221> NAME/KEY: gvpAPQBRNFGLSKJTU
<222> LOCATION: (1)..(7053)

<400> SEQUENCE: 11

```
gataaatttc gaaaggagct gctaaaaatg agtattcaaa aaagtacaga tagttctagt      60
ttagcagaag tgattgatcg aattctcgac aaagggattg tcatcgatgc ttttgcccga     120
gtatcactcg taggaattga aattttaacg attgaagcac gagtcgttat tgcaagtgtc     180
gatacgtggc ttcgctacgc agaagccgtt gggttattaa ccgacaaagt agaggaagaa     240
gggctgcctg gccgaacaga ggagcgagga gcagggctta gcttttaagt ctttaatcg      300 taagaaaatt cattaaataa ataataataa gagaaaagag gatgaaacat gtcaacaact     360
gataacaata tgcaaagtga aaacaagaa aatcagcagc aggaagaaaa aacgcaaaac      420 tcttaaatc ttgctatttt aggaggcgta gtaggagcgg gaattggact tctttcaagt     480
cctcaaacga gtaaaaaagt actcagccgc ttaggacaat cagaaattgt acgtgcgaca     540
ggacaagagt taagaagaaa cgcacaggat attctaacgc agcaagcgat gggagcatta     600
aggcagacgg ctacaggata tcttgaaaaa gacaattaa gcaagctgct ggcacctaaa      660
aagaaaaaag atgatgcatc aaatgaacag ggcgattcgc aggaagaagt cagccaaagc     720
gcagaaatgg aaacgtctca gtacgaagag ctaaagaag aaaataaaaa tatgaacgac      780
cagctgcagc gcattgaaga gatgctaaac aaactcatgg acgcgaagaa gtaagatatc     840
cgtcctgaag gggaatttca tggataaaaa agatgtggag aaagcagcct taaaagcagg     900 aaaaagatc atcgatcata cgcctgaacc tgttaaggaa aagatagaag aaaaggttaa      960
agaaaaagcg aaagaaaaat ttgtcgaaaa aactgaaggg aaactgcagg aaaaagcaaa    1020
tgaagcgtca gaaaaactgc aggaaacaaa agaaaaaaat gcccaaaagg tacacggcaa    1080
aggggaagac gcaaagaaaa gctccaaga cgtcttacta tcagtaaaag ataagcttag     1140
cgatgtgaaa gaagctggag aaaactttca gaaaaagtt tcttcttcag acgataaaga     1200
gaagtcaaaa aataagcgga aaataaaagg cgtaaatcag attaaaaaag caacggatat    1260
taaaagctct actaagatta aaagttctaa tgatattaaa tcatctacag atttaaaaac    1320
aatgggatca taagcgaaag gagaaatgag atatgtctat tcaaaaaagt actaatagtt    1380
caagtttagc agaagtcatt gaccgtattt tagataaagg aattgttatt gatgcttttg    1440
caagagtttc tgttgtagga attgaaattt taacgattga agcgcgagtg ttattgccca    1500
gtgttgatac atggttacgc tatgcagaag cagtagggct tcttcgtgac gacgtagaag    1560
aaaacggtct tcctgaacgt tcaaattcaa gtgaagggca gccgcgtttt agtatttaat    1620
```

```
atgaagtggt atggaacctt ccttttttga gggtggttcc agcttttaga tctaactatt    1680
ggaggctact aaaaatggaa attaaaaaaa ttatgcaagc cgtgaacgac tttttcggtg    1740
aacacgtagc tcctcctcat aaaattacct cggtggaagc tactgaagat gaaggttgga    1800
gagttattgt tgaagtcatt gaagaacgag aatatatgaa aaaatacgcc aaagatgaaa    1860
tgctcggaac gtacgagtgc tttgtaaata agaaaaaga agtcatttca ttcaaacgac    1920
tcgacgtcag atatagaagc gccattggca ttgaagcata acgataaga tggcaggagg     1980
aacgtaaaaa tgaccgtctt aacagacaaa aggaaaaaag gcagtggagc ttttatacaa    2040
gatgacgaga ccaaagaggt tctttcaaga gcgctgagct atttaaaatc cggctattcc    2100
attcatttta caggtcctgc cggcggaggc aaaacctctt tagcgcgagc gcttgctaaa    2160
aagagaaagc gtcctgtaat gctgatgcac gggaatcacg agctcaacaa caaagattta    2220
attggcgatt ttacgggata cacgagcaaa aaagtaatcg accagtacgt tcgttctgtc    2280
tataaaaaag atgaacaggt gagtgaaaac tggcaggatg gccgattgct tgaagctgta    2340
aaaaatggct atacgctgat ttacgacgaa tttactcgtt ctaagcctgc gacgaataat    2400
atctttctat cgatattaga agaaggcgtg ctgccgctgt atggagtaaa atgaccgat    2460
ccttttgtgc gcgtgcatcc cgatttccgc gtcatcttca caagcaatcc agctgagtat    2520
gccggcgtat atgatacgca agatgcgctt ctcgacaggt taattaccat gtttattgat    2580
tataaagaca tcgacagaga gacagcgatt ttaacggaga aaacggacgt agaagaagat    2640
gaagcgcgca caattgtaac gctcgtagca acgtgcgaa accgctctgg agacgaaaac    2700
agcagcggac ttagcctgcg ggcttcgctt atgatcgcta cccttgccac gcagcaagac    2760
attcctatcg atggaagtga cgaagatttt caaacgttat gtatcgatat tttgcatcat    2820
ccgcttacca aatgtttgga tgaagaaaat gcaaaaagca aagccgaaaa aatcatttta    2880
gaagaatgta agaatataga cactgaagaa aagtaaagga gcttgaaaac atgagtgaaa    2940
caaacgaaac aggtatttat attttttagcg ccattcaaac ggataaagac gaagaatttg    3000
gcgccgtgga agtagaagga acaaaagctg aaacatttt gattcgctac aaagacgcgg    3060
ctatggtagc agctgaagta ccgatgaaaa tttatcatcc taatcgccaa aatttattaa    3120
tgcatcaaaa cgcagtagca gcgattatgg acaagaacga tacggttatt ccaatcagct    3180
ttgggaatgt attcaaatca aagaagacg taaaagttct tttggaaaac ctttatccgc    3240
agtttgaaaa gctgtttcca gcgatcaaag gaaaaattga agtcggttta aaagtaattg    3300
ggaaaaaaga atggcttgag aaaaaagtaa acgaaaatcc tgaacttgag aaagtatcag    3360
catccgtaaa aggaaaatca gaagcagccg gttattatga gcgtattcaa cttggaggaa    3420
tggctcaaaa gatgtttact tccctgcaaa aagaagtcaa gacagatgtg ttttctccgc    3480
ttgaagaagc agcggaagca gcaaaagcaa atgagccaac gggcgaaacg atgcttttaa    3540
acgcgtcttt cttaattaac cgagaagatg aagcgaagtt tgatgaaaaa gtaaatgaag    3600
cgcatgaaaa ctggaaagac aaagccgatt ttcattacag cggtccttgg cctgcttata    3660
attttgtgaa cattcgccta aaagtagaag agaaataacg tgcttcacaa attagtaacc    3720
gcacccatta accttgtagt gaaaatcggc gaaaagtac aggaagaagc tgataaacag    3780
ctatatgacc ttccgacgat tcagcaaaag ctcattcagc ttcaaatgat gtttgagctt    3840
ggtgaaattc cagaagaagc gtttcaagaa aaagaagatg aattgttaat gaggtacgaa    3900
attgcgaaac gcagagaaat tgaacaatgg gaagagctaa cacaaaaaag aaatgaggaa    3960
tcctagatgg gagaattact gtatttatac ggtttaattc caacaaaaga agcagcagcc    4020
```

```
atagagccgt tccatttta taaggggttt gacggagaac attcactgta cccaattgcg    4080
tttgatcagg tgacggctgt agtttttaag ctgatgctg acacctattc agaaaaagtg    4140
attcaagaaa aaatggagca ggatatgagc tggctgcagg aaaaagcatt tcatcatcac    4200
gaaacggtag ccgctttgta cgaagaattt acgatcattc cattaaaatt ttgcaccatt    4260
tataaaggtg aagaaagtct gcaggcagct attgagatta caaagaaaa gatagagaat    4320 tcactgacgc tgcttcaagg aaatgaagag tggaatgtga aaatttactg tgatgataca    4380
gagcttaaaa aaggaatcag cgaaacgaat gaaagcgtga agcgaaaaa caagaaatt    4440 agtcacttat caccaggaag acagtttttt gaaagaaaaa aaatagatca gctgattgaa    4500
aaagaattag agcttcacaa aaacaaagtg tgtgaagaga tacatgacaa gctaatagaa    4560
ttatcgcttt atgactctgt taaaaagaat tggagcaaag acgtaactgg cgcagctgaa    4620
cagatggcgt ggaacagcgt gtttcttctc ccgtctctgc agattactaa gttcgtaaac    4680
gaaatagaag agcttcagca aaggcttgaa aataaaggct ggaagtttga agtgacggga    4740
ccatggccgc cctatcattt ctcgagcttt gcgtaaagtg aggaattaac attatgtctc    4800
ttaaacaatc catggagaat aaagatattg ctcttattga tatttagat gtcattttag    4860 ataaaggagt cgccattaaa ggagacttaa tcatttccat agctggcgtc gatttagtgt    4920
atttggattt gcgggtgctt atttcttcgg ttgaaacgct tgtgcaagca aaagaaggaa    4980
atcacaaacc aatcacttct gaacaatttg ataaacaaaa ggaggaatta atggatgcaa    5040
ccggtcagcc aagcaaatgg acgaatccac ttggatcctg atcaagctga acaaggctta    5100
gcgcagcttg tgatgacagt tattgagcta ttgaggcaaa tcgttgaacg tcatgccatg    5160
aggcgggtgg agggtggaac gttgacggac gaacaaattg aaaacttagg aattgcacta    5220
atgaacttag aagaaaaaat ggacgagttg aaagaggtgt tcggtctgga tgcagaagat    5280
ttaaatattg atcttggacc gctaggcagc ctgctttaag cggtcagtag gaggaacagt    5340
atggcagtcg aacataatat gcagtcaagt acgattgtag atgtgctcga aaagattttg    5400
gataaaggag tcgttatagc gggggacatc accgtaggaa ttgcagatgt cgagctatta    5460
acgattaaga tccgcttgat tgtggcttcg gttgataagg caaagaaat cggcatggac    5520 tggtgggaaa atgatccgta tctcagttca aaaggagcca ataacaaagc gctcgaagaa    5580
gaaaatanaa tgctgcatga gcggttaaaa acgcttgaag aaaaaataga aacgaaacgt    5640
taaaaactgt acgctactta aaaaatggag ggatttacaa tggcaactga acaaaatta    5700 gataacacac aggcagaaaa caaggaaaat aaaaatgcgg aaaacggttc aaaagaaaag    5760
aacggttcaa aagcaagcaa aacaacaagc agcgggccaa tcaaacgagc ggtagcagga    5820
ggcatcatcg gtcaacgat tggatatgta tcgactcctg aaaatcgaaa aagtctcctt    5880
gaccgcattg atacagacga attaaaaagc aaagcatctg atttaggaac aaaggtaaaa    5940
gaaaaatcaa aaagcagcgt ggccagcctg aaaacatctg cgggaagctt gtttaaaaaa    6000
gatgaagata aatcaaaaga tgatgaagaa aacgtaaatt cttctagtag cgaaacagaa    6060
gacgatgacg ttcaagagta cgacgagtta aagaagaaa atcaaactct tcaagatcgc    6120
ttatcacagc ttgaagaaaa aatgaacatg cttgttgagc ttagcctcaa taaaaatcaa    6180
gacgaagaag cggaagatac agattccgac gaagaagaga acgatgagaa cgatgaaaac    6240
gatgaaaacg agcaggacga tgaaaacgaa gaagaaacat ctaagccacg taaaaaggat    6300 aaaaagaag ctgaggaaga agaaagtgaa agtgacgaag acagcgagga agaagaggaa    6360
```

-continued

```
gattctcgct caaacaaaaa aaataaaaaa gtaaaaacag aagaagaaga cgaagatgaa    6420
agcgaagaag aaaaaaagga agcgaaaacca aaaaagtcaa cagctaaaaa atcaaaaaat   6480
acaaaagcaa agaaaaacac ggacgaagaa gatgatgaag caacatctct ttctagtgaa    6540
gacgatacaa cagcctaaga cgtaaaggag gaaagaaaga catgagtaca ggcccttctt    6600
tttcaactaa agacaatacg cttgaatact ttgtgaaagc ttctaataaa cacggctttt    6660
cacttgatat ttcattaaat gtaaacggcg ctgtgatttc cggtaccatg atttcagcaa    6720
aagaatactt tgattactta agcgaaacgt ttgaagaagg cagtgaagtg gctcaggcgc    6780
taagcgaaca attctcttta gcaagcgaag cgagcgaatc aaacggagaa gcagaagccc    6840
attttattca tttgaaaaat acaaagattt actgtggaga cagtaaatct actccttcta    6900
aaggcaaaat cttttggaga gggaaaatag cagaagtaga cgggttttttc ttaggaaaga   6960 tttctgatgc aaaatcaacg agtaaaaaga gttcataaaa aacggcgggg tgattgcccc    7020
gccgtttttt agtgatgtga tgagatgtgc agc                                 7053
```

<210> SEQ ID NO 12
<211> LENGTH: 13
<212> TYPE: PRT
<213> ORGANISM: Priestia megaterium
<220> FEATURE:
<221> NAME/KEY: first alpha helix
<222> LOCATION: (1)..(13)

<400> SEQUENCE: 12

Ser Ser Ser Leu Ala Glu Val Ile Asp Arg Ile Leu Asp
1               5                   10

<210> SEQ ID NO 13
<211> LENGTH: 13
<212> TYPE: PRT
<213> ORGANISM: Priestia megaterium
<220> FEATURE:
<221> NAME/KEY: first alpha helix
<222> LOCATION: (1)..(13)

<400> SEQUENCE: 13

Ser Ser Gly Leu Ala Glu Val Leu Asp Arg Val Leu Asp
1               5                   10

<210> SEQ ID NO 14
<211> LENGTH: 13
<212> TYPE: PRT
<213> ORGANISM: Priestia megaterium
<220> FEATURE:
<221> NAME/KEY: first beta sheet
<222> LOCATION: (1)..(13)

<400> SEQUENCE: 14

Lys Gly Ile Val Ile Asp Ala Phe Ala Arg Val Ser Leu
1               5                   10

<210> SEQ ID NO 15
<211> LENGTH: 13
<212> TYPE: PRT
<213> ORGANISM: Priestia megaterium
<220> FEATURE:
<221> NAME/KEY: first beta sheet
<222> LOCATION: (1)..(13)

<400> SEQUENCE: 15

Lys Gly Ile Val Ile Asp Ala Phe Ala Arg Val Ser Val
1               5                   10

<210> SEQ ID NO 16
<211> LENGTH: 13
<212> TYPE: PRT
<213> ORGANISM: Priestia megaterium
<220> FEATURE:
<221> NAME/KEY: first beta sheet
<222> LOCATION: (1)..(13)

<400> SEQUENCE: 16

Lys Gly Ile Val Ile Asp Ala Trp Val Arg Val Ser Leu
1               5                   10

<210> SEQ ID NO 17
<211> LENGTH: 13
<212> TYPE: PRT
<213> ORGANISM: Priestia megaterium
<220> FEATURE:
<221> NAME/KEY: first beta sheet
<222> LOCATION: (1)..(13)

<400> SEQUENCE: 17

Lys Gly Val Val Val Asp Val Trp Ala Arg Ile Ser Leu
1               5                   10

<210> SEQ ID NO 18
<211> LENGTH: 13
<212> TYPE: PRT
<213> ORGANISM: Priestia megaterium
<220> FEATURE:
<221> NAME/KEY: first beta sheet
<222> LOCATION: (1)..(13)

<400> SEQUENCE: 18

Lys Gly Val Val Val Asp Val Trp Ala Arg Val Ser Leu
1               5                   10

<210> SEQ ID NO 19
<211> LENGTH: 14
<212> TYPE: PRT
<213> ORGANISM: Priestia megaterium
<220> FEATURE:
<221> NAME/KEY: second beta sheet
<222> LOCATION: (1)..(14)

<400> SEQUENCE: 19

Val Gly Ile Glu Ile Leu Thr Ile Glu Ala Arg Val Val Ile
1               5                   10

<210> SEQ ID NO 20
<211> LENGTH: 14
<212> TYPE: PRT
<213> ORGANISM: Priestia megaterium
<220> FEATURE:
<221> NAME/KEY: second beta sheet
<222> LOCATION: (1)..(14)

<400> SEQUENCE: 20

Val Gly Ile Glu Leu Leu Ala Ile Glu Ala Arg Ile Val Ile
1               5                   10

<210> SEQ ID NO 21
<211> LENGTH: 14
<212> TYPE: PRT
<213> ORGANISM: Priestia megaterium
<220> FEATURE:
<221> NAME/KEY: second beta sheet
<222> LOCATION: (1)..(14)

<400> SEQUENCE: 21

Val Gly Ile Glu Ile Leu Thr Val Glu Ala Arg Val Val Ala
1               5                   10

<210> SEQ ID NO 22
<211> LENGTH: 13
<212> TYPE: PRT
<213> ORGANISM: Priestia megaterium
<220> FEATURE:
<221> NAME/KEY: second alpha helix
<222> LOCATION: (1)..(13)
<223> OTHER INFORMATION: Xaa is Ala or Glu; Glx is Val or Ile

<400> SEQUENCE: 22

Ala Ser Val Asp Thr Trp Leu Arg Tyr Ala Glu Xaa Glx
1               5                   10

<210> SEQ ID NO 23
<211> LENGTH: 13
<212> TYPE: PRT
<213> ORGANISM: PRIESTIA MEGATERIUM
<220> FEATURE:
<221> NAME/KEY: second alpha helix
<222> LOCATION: (1)..(13)
<223> OTHER INFORMATION: Xaa is Ala or Glu; Glx is Val or Ile

<400> SEQUENCE: 23

Ala Ser Val Glu Thr Tyr Leu Lys Tyr Ala Glu Xaa Glx
1               5                   10

<210> SEQ ID NO 24
<211> LENGTH: 13
<212> TYPE: PRT
<213> ORGANISM: Priestia megaterium
<220> FEATURE:
<221> NAME/KEY: second alpha helix
<222> LOCATION: (1)..(13)
<223> OTHER INFORMATION: Xaa is Ala or Glu; Glx is Val or Ile

<400> SEQUENCE: 24

Ala Ser Val Asp Thr Phe Leu His Tyr Ala Glu Xaa Glx
1               5                   10

<210> SEQ ID NO 25
<211> LENGTH: 33
<212> TYPE: PRT
<213> ORGANISM: Priestia megaterium
<220> FEATURE:
<221> NAME/KEY: Preserved GvpA C-terminus AA sequence
<222> LOCATION: (1)..(13)

<400> SEQUENCE: 25

Trp Leu Arg Tyr Ala Glu Ala Val Gly Leu Leu Thr Asp Lys Val Glu
1               5                   10                  15

Glu Glu Gly Leu Pro Gly Arg Thr Glu Glu Arg Gly Ala Gly Leu Ser
            20                  25                  30

Phe

<210> SEQ ID NO 26
<211> LENGTH: 27
<212> TYPE: PRT
<213> ORGANISM: Priestia megaterium
<220> FEATURE:
<221> NAME/KEY: Preserved GvpA C-terminus AA sequence
<222> LOCATION: (1)..(27)

```
<400> SEQUENCE: 26

Trp Leu Arg Tyr Ala Glu Ala Val Gly Leu Leu Thr Asp Lys Val Glu
1               5                   10                  15

Glu Glu Gly Leu Pro Gly Arg Thr Glu Glu Arg
            20                  25

<210> SEQ ID NO 27
<211> LENGTH: 23
<212> TYPE: PRT
<213> ORGANISM: Priestia megaterium
<220> FEATURE:
<221> NAME/KEY: Preserved GvpA C-terminus AA sequence
<222> LOCATION: (1)..(23)

<400> SEQUENCE: 27

Trp Leu Arg Tyr Ala Glu Ala Val Gly Leu Leu Thr Asp Lys Val Glu
1               5                   10                  15

Glu Glu Gly Leu Pro Gly Arg
            20

<210> SEQ ID NO 28
<211> LENGTH: 20
<212> TYPE: PRT
<213> ORGANISM: Priestia megaterium
<220> FEATURE:
<221> NAME/KEY: Preserved GvpA C-terminus AA sequence
<222> LOCATION: (1)..(20)

<400> SEQUENCE: 28

Trp Leu Arg Tyr Ala Glu Ala Val Gly Leu Leu Thr Asp Lys Val Glu
1               5                   10                  15

Glu Glu Gly Leu
            20

<210> SEQ ID NO 29
<211> LENGTH: 17
<212> TYPE: PRT
<213> ORGANISM: Priestia megaterium
<220> FEATURE:
<221> NAME/KEY: Preserved GvpA C-terminus AA sequence
<222> LOCATION: (1)..(17)

<400> SEQUENCE: 29

Trp Leu Arg Tyr Ala Glu Ala Val Gly Leu Leu Thr Asp Lys Val Glu
1               5                   10                  15

Glu

<210> SEQ ID NO 30
<211> LENGTH: 15
<212> TYPE: PRT
<213> ORGANISM: Priestia megaterium
<220> FEATURE:
<221> NAME/KEY: Preserved GvpA C-terminus AA sequence
<222> LOCATION: (1)..(15)

<400> SEQUENCE: 30

Trp Leu Arg Tyr Ala Glu Ala Val Gly Leu Leu Thr Asp Lys Val
1               5                   10                  15

<210> SEQ ID NO 31
<211> LENGTH: 14
<212> TYPE: PRT
<213> ORGANISM: Priestia megaterium
<220> FEATURE:
<221> NAME/KEY: Preserved GvpA C-terminus AA sequence
```

<222> LOCATION: (1)..(14)

<400> SEQUENCE: 31

Trp Leu Arg Tyr Ala Glu Ala Val Gly Leu Leu Thr Asp Lys
1               5                   10

<210> SEQ ID NO 32
<211> LENGTH: 13
<212> TYPE: PRT
<213> ORGANISM: Priestia megaterium
<220> FEATURE:
<221> NAME/KEY: Preserved GvpA C-terminus AA sequence
<222> LOCATION: (1)..(13)

<400> SEQUENCE: 32

Trp Leu Arg Tyr Ala Glu Ala Val Gly Leu Leu Thr Asp
1               5                   10

<210> SEQ ID NO 33
<211> LENGTH: 11
<212> TYPE: PRT
<213> ORGANISM: Priestia megaterium
<220> FEATURE:
<221> NAME/KEY: Preserved GvpA C-terminus AA sequence
<222> LOCATION: (1)..(11)

<400> SEQUENCE: 33

Trp Leu Arg Tyr Ala Glu Ala Val Gly Leu Leu
1               5                   10

<210> SEQ ID NO 34
<211> LENGTH: 9
<212> TYPE: PRT
<213> ORGANISM: Priestia megaterium
<220> FEATURE:
<221> NAME/KEY: Preserved GvpA C-terminus AA sequence
<222> LOCATION: (1)..(9)

<400> SEQUENCE: 34

Trp Leu Arg Tyr Ala Glu Ala Val Gly
1               5

<210> SEQ ID NO 35
<211> LENGTH: 8
<212> TYPE: PRT
<213> ORGANISM: Priestia megaterium
<220> FEATURE:
<221> NAME/KEY: Preserved GvpA C-terminus AA sequence
<222> LOCATION: (1)..(8)

<400> SEQUENCE: 35

Trp Leu Arg Tyr Ala Glu Ala Val
1               5

<210> SEQ ID NO 36
<211> LENGTH: 7
<212> TYPE: PRT
<213> ORGANISM: Priestia megaterium
<220> FEATURE:
<221> NAME/KEY: Preserved GvpA C-terminus AA sequence
<222> LOCATION: (1)..(7)

<400> SEQUENCE: 36

Trp Leu Arg Tyr Ala Glu Ala
1               5

<210> SEQ ID NO 37

```
<211> LENGTH: 6
<212> TYPE: PRT
<213> ORGANISM: Priestia megaterium
<220> FEATURE:
<221> NAME/KEY: Preserved GvpA C-terminus AA sequence
<222> LOCATION: (1)..(6)

<400> SEQUENCE: 37

Trp Leu Arg Tyr Ala Glu
1               5

<210> SEQ ID NO 38
<211> LENGTH: 5
<212> TYPE: PRT
<213> ORGANISM: Priestia megaterium
<220> FEATURE:
<221> NAME/KEY: Preserved GvpA C-terminus AA sequence
<222> LOCATION: (1)..(5)

<400> SEQUENCE: 38

Trp Leu Arg Tyr Ala
1               5

<210> SEQ ID NO 39
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 39

Thr Gly Cys Val Ile Ala Trp Asn Ser Asn Asn Leu Asp Ser
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 40

Asn Leu Asp Ser Lys Val Gly Gly Asn Tyr Asn Tyr Leu Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 41

Asn Tyr Leu Tyr Arg Leu Phe Arg Lys Ser Asn Leu Lys Pro
1               5                   10

<210> SEQ ID NO 42
<211> LENGTH: 14
<212> TYPE: PRT
<213> ORGANISM: Artificial Sequence
```

-continued

```
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 42

Asn Leu Lys Pro Phe Glu Arg Asp Ile Ser Thr Glu Ile Tyr
1               5                   10

<210> SEQ ID NO 43
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 43

Thr Glu Ile Tyr Gln Ala Gly Ser Thr Pro Cys Asn Gly Val
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 44

Cys Asn Gly Val Glu Gly Phe Asn Cys Tyr Phe Pro Leu Gln
1               5                   10

<210> SEQ ID NO 45
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 45

Phe Pro Leu Gln Ser Tyr Gly Phe Gln Pro Thr Asn Gly Val
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: Heterologous Peptide Sequences
<222> LOCATION: (1)..(14)

<400> SEQUENCE: 46

Thr Asn Gly Val Gly Tyr Gln Pro Tyr Arg Val Val Val Leu
1               5                   10

<210> SEQ ID NO 47
<211> LENGTH: 70
<212> TYPE: PRT
```

<213> ORGANISM: Anabaena flosaquae
<220> FEATURE:
<221> NAME/KEY: Major rib protein
<222> LOCATION: (1)..(70)

<400> SEQUENCE: 47

Ala Val Glu Lys Thr Asn Ser Ser Ser Leu Ala Glu Val Ile Asp
1               5                   10                  15

Arg Ile Leu Asp Lys Gly Ile Val Ile Asp Ala Trp Val Arg Val Ser
                20                  25                  30

Leu Val Gly Ile Glu Leu Leu Ala Ile Glu Ala Arg Ile Val Ile Ala
            35                  40                  45

Ser Val Glu Thr Tyr Leu Lys Tyr Ala Glu Ala Val Gly Leu Thr Gln
    50                  55                  60

Ser Ala Ala Val Pro Ala
65                  70

<210> SEQ ID NO 48
<211> LENGTH: 79
<212> TYPE: PRT
<213> ORGANISM: Halobacterium salinarum
<220> FEATURE:
<221> NAME/KEY: c-vac
<222> LOCATION: (1)..(79)

<400> SEQUENCE: 48

Met Ala Gln Pro Asp Ser Ser Leu Ala Glu Val Leu Asp Arg Val
1               5                   10                  15

Leu Asp Lys Gly Val Val Val Asp Val Trp Ala Arg Ile Ser Leu Val
                20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
    50                  55                  60

Glu Leu Thr Ala Gly Ala Glu Ala Pro Glu Pro Ala Pro Glu Ala
65                  70                  75

<210> SEQ ID NO 49
<211> LENGTH: 85
<212> TYPE: PRT
<213> ORGANISM: Halobacterium salinarum
<220> FEATURE:
<221> NAME/KEY: p-vac
<222> LOCATION: (1)..(85)

<400> SEQUENCE: 49

Met Ala Gln Pro Asp Ser Ser Gly Leu Ala Glu Val Leu Asp Arg Val
1               5                   10                  15

Leu Asp Lys Gly Val Val Val Asp Val Trp Ala Arg Val Ser Leu Val
                20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
    50                  55                  60

Glu Leu Thr Ala Gly Ala Arg Arg His Pro Arg Pro Asp Ala Gln Ala
65                  70                  75                  80

Ser Leu Arg Pro Ala
                85

<210> SEQ ID NO 50

```
<211> LENGTH: 88
<212> TYPE: PRT
<213> ORGANISM: Artificial Sequence
<220> FEATURE:
<223> OTHER INFORMATION: synthetic construct
<220> FEATURE:
<221> NAME/KEY: minor rib protein with heterologous peptide
<222> LOCATION: (1)..(88)
<223> OTHER INFORMATION: Xaa residues represent the heterologous peptide
      sequence

<400> SEQUENCE: 50

Met Ser Ile Gln Lys Ser Thr Asp Ser Ser Ser Leu Ala Glu Val Ile
1               5                   10                  15

Asp Arg Ile Leu Asp Lys Gly Ile Val Ile Asp Ala Phe Ala Arg Val
            20                  25                  30

Ser Leu Val Gly Ile Glu Ile Leu Thr Ile Glu Ala Arg Val Val Ile
                35                  40                  45

Ala Ser Val Asp Thr Trp Leu Arg Tyr Ala Glu Ala Val Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
                85

<210> SEQ ID NO 51
<211> LENGTH: 88
<212> TYPE: PRT
<213> ORGANISM: Artificial Sequence
<220> FEATURE:
<223> OTHER INFORMATION: synthetic construct
<220> FEATURE:
<221> NAME/KEY: minor rib protein with heterologous peptide
<222> LOCATION: (1)..(88)
<223> OTHER INFORMATION: Xaa residues represent the heterologous peptide
      sequence

<400> SEQUENCE: 51

Met Ser Ile Gln Lys Ser Thr Asn Ser Ser Ser Leu Ala Glu Val Ile
1               5                   10                  15

Asp Arg Ile Leu Asp Lys Gly Ile Val Ile Asp Ala Phe Ala Arg Val
            20                  25                  30

Ser Val Val Gly Ile Glu Ile Leu Thr Ile Glu Ala Arg Val Val Ile
                35                  40                  45

Ala Ser Val Asp Thr Trp Leu Arg Tyr Ala Glu Ala Val Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
                85
```